(12) United States Patent
Mortier et al.

(10) Patent No.: US 8,226,711 B2
(45) Date of Patent: Jul. 24, 2012

(54) VALVE TO MYOCARDIUM TENSION MEMBERS DEVICE AND METHOD

(75) Inventors: Todd J. Mortier, Minneapolis, MN (US); Cyril J. Schweich, Jr., St. Paul, MN (US)

(73) Assignee: Edwards Lifesciences, LLC, Irvine, CA (US)

( * ) Notice: Subject to any disclaimer, the term of this patent is extended or adjusted under 35 U.S.C. 154(b) by 1625 days.

(21) Appl. No.: 11/172,437

(22) Filed: Jul. 1, 2005

(65) Prior Publication Data

US 2006/0052868 A1 Mar. 9, 2006

Related U.S. Application Data

(63) Continuation of application No. 09/981,790, filed on Oct. 19, 2001, which is a continuation of application No. 08/992,316, filed on Dec. 17, 1997, now Pat. No. 6,332,893.

(51) Int. Cl.
*A61F 2/24* (2006.01)
*A61F 2/82* (2006.01)

(52) U.S. Cl. ........................ 623/2.36; 623/900

(58) Field of Classification Search ............. 623/2.1, 623/2.36, 2.37, 3.1, 23.64, 904, 900; 600/37
See application file for complete search history.

(56) References Cited

U.S. PATENT DOCUMENTS

| | | |
|---|---|---|
| 963,899 A | 7/1910 | Kistler |
| 3,019,790 A | 2/1962 | Militana |
| 3,656,185 A | 4/1972 | Carpentier |
| 3,980,086 A | 9/1976 | Kletschka et al. |
| 4,035,849 A | 7/1977 | Angell et al. |
| 4,055,861 A | 11/1977 | Carpentier et al. |
| 4,192,293 A | 3/1980 | Asrican |
| 4,217,665 A | 8/1980 | Bex et al. |
| 4,261,342 A | 4/1981 | Aranguren Duo |
| 4,300,564 A | 11/1981 | Furihata |
| 4,306,319 A | 12/1981 | Kaster |
| 4,343,048 A | 8/1982 | Ross et al. |
| 4,372,293 A | 2/1983 | Vijil-Rosales |
| 4,409,974 A | 10/1983 | Freedland |
| 4,536,893 A | 8/1985 | Parravicini |
| 4,579,120 A | 4/1986 | MacGregor |

(Continued)

FOREIGN PATENT DOCUMENTS

DE 32 27 984 A1 2/1984

(Continued)

OTHER PUBLICATIONS

Edie, M.D. et al., "Surgical repair of single ventricle," *The Journal of Thoracic and Cardiovascular Surgery*, Sep. 1973, pp. 350-360, vol. 66, No. 3, Mosby-Year Book, Inc.

(Continued)

*Primary Examiner* — David H. Willse
(74) *Attorney, Agent, or Firm* — AnnMarie Kaiser; Guy Cumberbatch (57) ABSTRACT

A device for heart valve repair including at least one tension member having a first end and second end. A basal anchor is disposed at the first end of the tension member and a secondary anchor at the second end. The method includes the steps of anchoring the basal anchor proximate a heart valve and anchoring the secondary anchor at a location spaced from the valve such that the chamber geometry is altered to reduce heart wall tension and/or stress on the valve leaflets.

35 Claims, 7 Drawing Sheets

U.S. PATENT DOCUMENTS

| | | | |
|---|---|---|---|
| 4,592,342 A | 6/1986 | Salmasian |
| 4,629,459 A | 12/1986 | Ionescu et al. |
| 4,632,101 A | 12/1986 | Freedland |
| 4,690,134 A | 9/1987 | Snyders |
| 4,705,040 A | 11/1987 | Mueller et al. |
| 4,936,857 A | 6/1990 | Kulik |
| 4,944,753 A | 7/1990 | Burgess et al. |
| 4,960,424 A | 10/1990 | Grooters |
| 4,991,578 A | 2/1991 | Cohen |
| 4,997,431 A | 3/1991 | Isner et al. |
| 5,061,277 A | 10/1991 | Carpentier et al. |
| 5,104,407 A | 4/1992 | Lam et al. |
| 5,106,386 A | 4/1992 | Isner et al. |
| 5,131,905 A | 7/1992 | Grooters |
| RE34,021 E | 8/1992 | Mueller et al. |
| 5,152,765 A | 10/1992 | Ross et al. |
| 5,156,621 A | 10/1992 | Navia et al. |
| 5,169,381 A | 12/1992 | Snyders |
| 5,192,314 A | 3/1993 | Daskalakis |
| 5,250,049 A | 10/1993 | Michael |
| 5,256,132 A | 10/1993 | Snyders |
| 5,258,015 A | 11/1993 | Li et al. |
| 5,284,488 A | 2/1994 | Sideris |
| 5,300,087 A | 4/1994 | Knoepfler |
| 5,312,642 A | 5/1994 | Chesterfield et al. |
| 5,360,444 A | 11/1994 | Kusuhara |
| 5,376,112 A | 12/1994 | Duren |
| 5,383,840 A | 1/1995 | Heilman et al. |
| 5,385,528 A | 1/1995 | Wilk |
| 5,389,096 A | 2/1995 | Aita et al. |
| 5,397,331 A | 3/1995 | Himpens et al. |
| 5,417,709 A | 5/1995 | Slater |
| 5,433,727 A | 7/1995 | Sideris |
| 5,445,600 A | 8/1995 | Abdulla |
| 5,450,860 A | 9/1995 | O'Connor |
| 5,452,733 A | 9/1995 | Sterman et al. |
| 5,458,574 A | 10/1995 | Machold et al. |
| 5,496,305 A | 3/1996 | Kittrell et al. |
| 5,509,428 A | 4/1996 | Dunlop |
| 5,522,884 A | 6/1996 | Wright |
| 5,533,958 A | 7/1996 | Wilk |
| 5,571,215 A | 11/1996 | Sterman et al. |
| 5,584,803 A | 12/1996 | Stevens et al. |
| 5,593,424 A | 1/1997 | Northrup, III |
| 5,607,471 A | 3/1997 | Seguin et al. |
| 5,655,548 A | 8/1997 | Nelson et al. |
| 5,665,092 A | 9/1997 | Mangiardi et al. |
| 5,674,279 A | 10/1997 | Wright et al. |
| 5,682,906 A | 11/1997 | Sterman et al. |
| 5,702,343 A | 12/1997 | Alferness |
| 5,713,954 A | 2/1998 | Rosenberg et al. |
| 5,718,725 A | 2/1998 | Sterman et al. |
| 5,738,649 A | 4/1998 | Macoviak |
| 5,755,783 A | 5/1998 | Stobie et al. |
| 5,758,663 A | 6/1998 | Wilk et al. |
| 5,766,234 A | 6/1998 | Chen et al. |
| 5,776,189 A | 7/1998 | Khalid et al. |
| 5,800,334 A | 9/1998 | Wilk |
| 5,800,528 A | 9/1998 | Lederman et al. |
| 5,800,531 A | 9/1998 | Cosgrove et al. |
| 5,807,384 A | 9/1998 | Mueller |
| 5,814,097 A | 9/1998 | Sterman et al. |
| 5,824,066 A | 10/1998 | Gross |
| 5,824,069 A | 10/1998 | Lemole |
| 5,840,059 A | 11/1998 | March et al. |
| 5,849,005 A | 12/1998 | Garrison et al. |
| 5,855,601 A | 1/1999 | Bessler et al. |
| 5,855,614 A | 1/1999 | Stevens et al. |
| 5,865,791 A | 2/1999 | Whayne et al. |
| 5,876,436 A | 3/1999 | Vanney et al. |
| 5,888,240 A | 3/1999 | Carpentier et al. |
| 5,902,229 A | 5/1999 | Tsitlik et al. |
| 5,928,281 A | 7/1999 | Huynh et al. |
| 5,944,738 A | 8/1999 | Amplatz et al. |
| 5,957,977 A | 9/1999 | Melvin |
| 5,961,440 A | 10/1999 | Schweich, Jr. et al. |
| 5,961,539 A | 10/1999 | Northrup, III et al. |
| 5,961,549 A | 10/1999 | Nguyen et al. |
| 5,967,990 A | 10/1999 | Thierman et al. |
| 5,971,910 A | 10/1999 | Tsitlik et al. |
| 5,971,911 A | 10/1999 | Wilk |
| 5,972,022 A | 10/1999 | Huxel |
| 5,972,030 A | 10/1999 | Garrison et al. |
| 5,984,857 A | 11/1999 | Buck et al. |
| 5,984,917 A | 11/1999 | Fleischman et al. |
| 5,999,678 A | 12/1999 | Murphy-Chutorian et al. |
| 6,001,126 A | 12/1999 | Nguyen-Thien-Nhon |
| 6,019,722 A | 2/2000 | Spence et al. |
| 6,024,096 A | 2/2000 | Buckberg |
| 6,024,756 A | 2/2000 | Huebsch et al. |
| 6,045,497 A | 4/2000 | Schweich, Jr. et al. |
| 6,050,936 A | 4/2000 | Schweich, Jr. et al. |
| 6,059,715 A | 5/2000 | Schweich, Jr. et al. |
| 6,071,303 A | 6/2000 | Laufer |
| 6,077,214 A | 6/2000 | Mortier et al. |
| 6,077,218 A | 6/2000 | Alferness |
| 6,079,414 A | 6/2000 | Roth |
| 6,085,754 A | 7/2000 | Alferness et al. |
| 6,086,532 A | 7/2000 | Panescu et al. |
| 6,095,968 A | 8/2000 | Snyders |
| 6,102,944 A | 8/2000 | Huynh et al. |
| 6,110,100 A | 8/2000 | Talpade |
| 6,113,536 A | 9/2000 | Aboul-Hosn et al. |
| 6,113,636 A | 9/2000 | Ogle |
| 6,117,159 A | 9/2000 | Huebsch et al. |
| 6,120,520 A | 9/2000 | Saadat et al. |
| 6,123,662 A | 9/2000 | Alferness et al. |
| 6,125,852 A | 10/2000 | Stevens et al. |
| 6,126,590 A | 10/2000 | Alferness |
| 6,129,758 A | 10/2000 | Love |
| 6,132,438 A | 10/2000 | Fleischman et al. |
| 6,143,025 A | 11/2000 | Stobie et al. |
| 6,155,968 A | 12/2000 | Wilk |
| 6,155,972 A | 12/2000 | Nauertz et al. |
| 6,162,168 A | 12/2000 | Schweich, Jr. et al. |
| 6,165,119 A | 12/2000 | Schweich, Jr. et al. |
| 6,165,120 A | 12/2000 | Schweich, Jr. et al. |
| 6,165,121 A | 12/2000 | Alferness |
| 6,165,122 A | 12/2000 | Alferness |
| 6,165,183 A | 12/2000 | Kuehn et al. |
| 6,169,922 B1 | 1/2001 | Alferness et al. |
| 6,174,279 B1 | 1/2001 | Girard |
| 6,174,332 B1 | 1/2001 | Loch et al. |
| 6,179,791 B1 | 1/2001 | Krueger |
| 6,182,664 B1 | 2/2001 | Cosgrove |
| 6,183,411 B1 | 2/2001 | Mortier et al. |
| 6,183,512 B1 | 2/2001 | Howanec, Jr. et al. |
| 6,190,408 B1 | 2/2001 | Malvin |
| 6,193,648 B1 | 2/2001 | Krueger |
| 6,197,053 B1 | 3/2001 | Cosgrove et al. |
| 6,206,004 B1 | 3/2001 | Schmidt et al. |
| 6,206,820 B1 | 3/2001 | Kazi et al. |
| 6,210,432 B1 | 4/2001 | Solem et al. |
| 6,217,610 B1 | 4/2001 | Carpentier et al. |
| 6,221,013 B1 | 4/2001 | Panescu et al. |
| 6,221,103 B1 | 4/2001 | Melvin |
| 6,221,104 B1 | 4/2001 | Buckberg et al. |
| 6,224,540 B1 | 5/2001 | Lederman et al. |
| 6,230,714 B1 | 5/2001 | Alferness et al. |
| 6,231,561 B1 | 5/2001 | Frazier et al. |
| 6,231,602 B1 | 5/2001 | Carpentier et al. |
| 6,238,334 B1 | 5/2001 | Easterbrook, III et al. |
| 6,241,654 B1 | 6/2001 | Alferness |
| 6,245,102 B1 | 6/2001 | Jayaraman |
| 6,245,105 B1 | 6/2001 | Nguyen et al. |
| 6,250,308 B1 | 6/2001 | Cox |
| 6,251,061 B1 | 6/2001 | Hastings et al. |
| 6,258,021 B1 | 7/2001 | Wilk |
| 6,258,023 B1 | 7/2001 | Rogers et al. |
| 6,260,552 B1 | 7/2001 | Mortier et al. |
| 6,260,820 B1 | 7/2001 | Chowdhury |
| 6,261,222 B1 | 7/2001 | Schweich, Jr. et al. |
| 6,264,602 B1 | 7/2001 | Mortier et al. |
| 6,269,819 B1 | 8/2001 | Oz et al. |
| 6,283,993 B1 | 9/2001 | Cosgrove et al. |
| 6,290,674 B1 | 9/2001 | Roue et al. |
| 6,293,906 B1 | 9/2001 | Vanden Hoek et al. |

| | | |
|---|---|---|
| 6,309,370 B1 | 10/2001 | Haim et al. |
| 6,312,447 B1 | 11/2001 | Grimes |
| 6,314,322 B1 | 11/2001 | Rosenberg |
| 6,328,727 B1 | 12/2001 | Frazier et al. |
| 6,331,157 B2 | 12/2001 | Hancock |
| 6,332,863 B1 | 12/2001 | Schweich, Jr. et al. |
| 6,332,864 B1 | 12/2001 | Schweich, Jr. et al. |
| 6,332,893 B1 | 12/2001 | Mortier et al. |
| 6,338,712 B2 | 1/2002 | Spence et al. |
| 6,343,605 B1 | 2/2002 | Lafontaine |
| 6,360,749 B1 | 3/2002 | Jayaraman |
| 6,361,545 B1 | 3/2002 | Macoviak |
| 6,370,429 B1 | 4/2002 | Alferness et al. |
| 6,375,608 B1 | 4/2002 | Alferness |
| 6,379,366 B1 | 4/2002 | Fleischman et al. |
| 6,402,679 B1 | 6/2002 | Mortier et al. |
| 6,402,680 B2 | 6/2002 | Mortier et al. |
| 6,402,781 B1 | 6/2002 | Langberg et al. |
| 6,406,420 B1 | 6/2002 | McCarthy et al. |
| 6,406,422 B1 | 6/2002 | Landesberg |
| 6,409,759 B1 | 6/2002 | Peredo |
| 6,409,760 B1 | 6/2002 | Melvin |
| 6,416,459 B1 | 7/2002 | Haindl |
| 6,419,669 B1 | 7/2002 | Frazier et al. |
| 6,425,856 B1 | 7/2002 | Shapland et al. |
| 6,432,039 B1 | 8/2002 | Wardle |
| 6,432,059 B2 | 8/2002 | Hickey |
| 6,436,088 B2 | 8/2002 | Frazier et al. |
| 6,439,237 B1 | 8/2002 | Buckberg et al. |
| 6,443,949 B2 | 9/2002 | Altman |
| 6,450,171 B1 | 9/2002 | Buckberg et al. |
| 6,458,100 B2 | 10/2002 | Roue et al. |
| 6,461,366 B1 | 10/2002 | Seguin |
| 6,478,729 B1 | 11/2002 | Rogers et al. |
| 6,482,146 B1 | 11/2002 | Alferness et al. |
| 6,488,706 B1 | 12/2002 | Solymar |
| 6,494,825 B1 | 12/2002 | Talpade |
| 6,511,426 B1 | 1/2003 | Hossack et al. |
| 8,756,131 | 1/2003 | Kung et al. |
| 6,514,194 B2 | 2/2003 | Schweich, Jr. et al. |
| 6,520,904 B1 | 2/2003 | Melvin |
| 6,537,198 B1 | 3/2003 | Vidlund et al. |
| 6,537,203 B1 | 3/2003 | Alferness et al. |
| 6,537,314 B2 | 3/2003 | Langberg et al. |
| 6,544,167 B2 | 4/2003 | Buckberg et al. |
| 6,544,180 B1 | 4/2003 | Doten et al. |
| 6,547,821 B1 | 4/2003 | Taylor et al. |
| 6,569,198 B1 | 5/2003 | Wilson et al. |
| 6,572,529 B2 | 6/2003 | Wilk |
| 6,582,355 B2 | 6/2003 | Alferness et al. |
| 6,587,734 B2 | 7/2003 | Okuzumi |
| 6,589,160 B2 | 7/2003 | Schweich, Jr. et al. |
| 6,592,619 B2 | 7/2003 | Melvin |
| 6,595,912 B2 | 7/2003 | Lau et al. |
| 6,602,182 B1 | 8/2003 | Milbocker |
| 6,602,184 B2 | 8/2003 | Lau et al. |
| 6,612,278 B2 | 9/2003 | Kampichler |
| 6,612,978 B2 | 9/2003 | Lau et al. |
| 6,612,979 B2 | 9/2003 | Lau et al. |
| 6,616,596 B1 | 9/2003 | Milbocker |
| 6,616,684 B1 | 9/2003 | Vidlund et al. |
| 6,619,291 B2 | 9/2003 | Hlavka |
| 6,622,730 B2 | 9/2003 | Ekvall et al. |
| 6,626,821 B1 | 9/2003 | Kung et al. |
| 6,626,930 B1 | 9/2003 | Allen et al. |
| 6,629,534 B1 | 10/2003 | St. Goar et al. |
| 6,629,921 B1 | 10/2003 | Schweich, Jr. et al. |
| 6,645,139 B2 | 11/2003 | Haindl |
| 6,651,671 B1 | 11/2003 | Donlon et al. |
| 6,656,221 B2 | 12/2003 | Taylor et al. |
| 6,663,558 B2 | 12/2003 | Lau et al. |
| 6,673,009 B1 | 1/2004 | Vanden Hoek et al. |
| 6,676,702 B2 | 1/2004 | Mathis |
| 6,681,773 B2 | 1/2004 | Murphy et al. |
| 6,682,474 B2 | 1/2004 | Lau et al. |
| 6,682,475 B2 | 1/2004 | Cox et al. |
| 6,682,476 B2 | 1/2004 | Alferness et al. |
| 6,685,620 B2 | 2/2004 | Gifford, III et al. |
| 6,685,627 B2 | 2/2004 | Jayaraman |
| 6,685,646 B2 | 2/2004 | Cespedes et al. |
| 6,689,048 B2 | 2/2004 | Vanden Hoek et al. |
| 6,695,768 B1 | 2/2004 | Levine et al. |
| 6,695,866 B1 | 2/2004 | Kuehn et al. |
| 6,701,929 B2 | 3/2004 | Hussein |
| 6,702,732 B1 | 3/2004 | Lau et al. |
| 6,702,763 B2 | 3/2004 | Murphy et al. |
| 6,702,826 B2 | 3/2004 | Liddicoat et al. |
| 6,706,065 B2 | 3/2004 | Langberg et al. |
| 6,709,456 B2 | 3/2004 | Langberg et al. |
| 6,712,804 B2 | 3/2004 | Roue et al. |
| 6,716,158 B2 | 4/2004 | Raman et al. |
| 6,719,767 B1 | 4/2004 | Kimblad |
| 6,723,038 B1 | 4/2004 | Schroeder et al. |
| 6,726,716 B2 | 4/2004 | Marquez |
| 6,726,717 B2 | 4/2004 | Alfieri et al. |
| 6,730,016 B1 | 5/2004 | Cox et al. |
| 6,733,525 B2 | 5/2004 | Yang et al. |
| 6,740,107 B2 | 5/2004 | Loeb et al. |
| 6,752,813 B2 | 6/2004 | Goldfarb et al. |
| 6,755,777 B2 | 6/2004 | Schweich, Jr. et al. |
| 6,755,779 B2 | 6/2004 | Vanden Hoek et al. |
| 6,767,362 B2 | 7/2004 | Schreck |
| 6,769,434 B2 | 8/2004 | Liddicoat et al. |
| 6,776,754 B1 | 8/2004 | Wilk |
| 6,790,231 B2 | 9/2004 | Liddicoat et al. |
| 6,793,673 B2 | 9/2004 | Kowalsky et al. |
| 6,797,001 B2 | 9/2004 | Mathis et al. |
| 6,800,090 B2 | 10/2004 | Alferness et al. |
| 6,805,710 B2 | 10/2004 | Bolling et al. |
| 6,810,882 B2 | 11/2004 | Langberg et al. |
| 6,814,700 B1 | 11/2004 | Mueller et al. |
| 6,824,562 B2 | 11/2004 | Mathis et al. |
| 6,830,585 B1 | 12/2004 | Artof et al. |
| 6,837,247 B2 | 1/2005 | Buckberg et al. |
| 6,846,296 B1 | 1/2005 | Milbocker et al. |
| 6,858,039 B2 | 2/2005 | McCarthy |
| 6,875,224 B2 | 4/2005 | Grimes |
| 6,876,887 B2 | 4/2005 | Okuzumi |
| 6,881,185 B2 | 4/2005 | Vanden Hock et al. |
| 6,887,192 B1 | 5/2005 | Whayne et al. |
| 6,890,353 B2 | 5/2005 | Cohn et al. |
| 6,893,392 B2 | 5/2005 | Alferness |
| 6,896,652 B2 | 5/2005 | Alferness et al. |
| 6,902,522 B1 | 6/2005 | Walsh et al. |
| 6,908,426 B2 | 6/2005 | Shapland et al. |
| 6,908,478 B2 | 6/2005 | Alferness et al. |
| 6,913,608 B2 | 7/2005 | Liddicoat et al. |
| 6,918,917 B1 | 7/2005 | Nguyen et al. |
| 6,921,407 B2 | 7/2005 | Nguyen et al. |
| 6,949,122 B2 | 9/2005 | Adams et al. |
| 6,951,534 B2 | 10/2005 | Girard et al. |
| 6,955,689 B2 | 10/2005 | Ryan et al. |
| 6,959,711 B2 | 11/2005 | Murphy et al. |
| 6,960,229 B2 | 11/2005 | Mathis et al. |
| 6,962,605 B2 | 11/2005 | Cosgrove et al. |
| 6,966,926 B2 | 11/2005 | Mathis |
| 6,976,995 B2 | 12/2005 | Mathis et al. |
| 7,163,507 B2 | 1/2007 | Alferness |
| 7,166,071 B2 | 1/2007 | Alferness |
| 7,189,199 B2 | 3/2007 | McCarthy et al. |
| 7,255,674 B2 | 8/2007 | Alferness |
| 7,261,684 B2 | 8/2007 | Alferness |
| 7,278,964 B2 | 10/2007 | Alferness |
| 7,351,200 B2 | 4/2008 | Alferness |
| 2001/0003986 A1 | 6/2001 | Cosgrove |
| 2001/0005787 A1 | 6/2001 | Oz et al. |
| 2001/0009976 A1 | 7/2001 | Panescu et al. |
| 2001/0014800 A1 | 8/2001 | Frazier et al. |
| 2001/0014811 A1 | 8/2001 | Hussein |
| 2001/0018611 A1 | 8/2001 | Solem et al. |
| 2001/0021874 A1 | 9/2001 | Carpentier et al. |
| 2001/0029314 A1 | 10/2001 | Alferness et al. |
| 2001/0034551 A1 | 10/2001 | Cox |
| 2001/0037123 A1 | 11/2001 | Hancock |
| 2001/0039434 A1 | 11/2001 | Frazier et al. |
| 2001/0039435 A1 | 11/2001 | Roue et al. |
| 2001/0039436 A1 | 11/2001 | Frazier et al. |
| 2001/0041821 A1 | 11/2001 | Wilk |

| Pub. No. | Date | Inventor |
|---|---|---|
| 2001/0041914 A1 | 11/2001 | Frazier et al. |
| 2001/0041915 A1 | 11/2001 | Roue et al. |
| 2001/0044568 A1 | 11/2001 | Langberg et al. |
| 2001/0047122 A1 | 11/2001 | Vanden Hoek et al. |
| 2001/0049492 A1 | 12/2001 | Frazier et al. |
| 2002/0007216 A1 | 1/2002 | Melvin |
| 2002/0013571 A1 | 1/2002 | Goldfarb et al. |
| 2002/0016628 A1 | 2/2002 | Langberg et al. |
| 2002/0019580 A1 | 2/2002 | Lau et al. |
| 2002/0022880 A1 | 2/2002 | Melvin |
| 2002/0026092 A1 | 2/2002 | Buckberg et al. |
| 2002/0028981 A1 | 3/2002 | Lau et al. |
| 2002/0029783 A1 | 3/2002 | Stevens et al. |
| 2002/0032364 A1 | 3/2002 | Lau et al. |
| 2002/0042554 A1 | 4/2002 | Alferness et al. |
| 2002/0045798 A1 | 4/2002 | Lau et al. |
| 2002/0045799 A1 | 4/2002 | Lau et al. |
| 2002/0045800 A1 | 4/2002 | Lau et al. |
| 2002/0052538 A1 | 5/2002 | Lau et al. |
| 2002/0056461 A1 | 5/2002 | Jayaraman |
| 2002/0058855 A1 | 5/2002 | Schweich, Jr. et al. |
| 2002/0065449 A1 | 5/2002 | Wardle |
| 2002/0065465 A1 | 5/2002 | Panescu et al. |
| 2002/0065554 A1 | 5/2002 | Streeter |
| 2002/0068850 A1 | 6/2002 | Vanden Hoek et al. |
| 2002/0077532 A1 | 6/2002 | Gannoe et al. |
| 2002/0082647 A1 | 6/2002 | Alferness et al. |
| 2002/0087173 A1 | 7/2002 | Alferness et al. |
| 2002/0091296 A1 | 7/2002 | Alferness |
| 2002/0103511 A1 | 8/2002 | Alferness et al. |
| 2002/0103532 A1 | 8/2002 | Langberg et al. |
| 2002/0103533 A1 | 8/2002 | Langberg et al. |
| 2002/0111533 A1 | 8/2002 | Melvin |
| 2002/0111567 A1 | 8/2002 | Vanden Hoek et al. |
| 2002/0111636 A1 | 8/2002 | Fleischman et al. |
| 2002/0133055 A1 | 9/2002 | Haindl |
| 2002/0143250 A1 | 10/2002 | Panescu et al. |
| 2002/0151766 A1 | 10/2002 | Shapland et al. |
| 2002/0151961 A1 | 10/2002 | Lashinski et al. |
| 2002/0161275 A1 | 10/2002 | Schweich, Jr. et al. |
| 2002/0169358 A1 | 11/2002 | Mortier et al. |
| 2002/0169359 A1 | 11/2002 | McCarthy et al. |
| 2002/0169360 A1 | 11/2002 | Taylor et al. |
| 2002/0169502 A1 | 11/2002 | Mathis |
| 2002/0169504 A1 | 11/2002 | Alferness et al. |
| 2002/0173694 A1 | 11/2002 | Mortier et al. |
| 2002/0183835 A1 | 12/2002 | Taylor et al. |
| 2002/0183836 A1 | 12/2002 | Liddicoat et al. |
| 2002/0183837 A1 | 12/2002 | Streeter et al. |
| 2002/0183838 A1 | 12/2002 | Liddicoat et al. |
| 2002/0183841 A1 | 12/2002 | Cohn et al. |
| 2002/0188170 A1 | 12/2002 | Santamore et al. |
| 2002/0188350 A1 | 12/2002 | Arru et al. |
| 2003/0004396 A1 | 1/2003 | Vanden Hock et al. |
| 2003/0009081 A1 | 1/2003 | Rogers et al. |
| 2003/0023132 A1 | 1/2003 | Melvin et al. |
| 2003/0028077 A1 | 2/2003 | Alferness et al. |
| 2003/0032979 A1 | 2/2003 | Mortier et al. |
| 2003/0045771 A1 | 3/2003 | Schweich, Jr. et al. |
| 2003/0045776 A1 | 3/2003 | Alferness et al. |
| 2003/0045896 A1 | 3/2003 | Murphy et al. |
| 2003/0050529 A1 | 3/2003 | Vidlund et al. |
| 2003/0050659 A1 | 3/2003 | Murphy et al. |
| 2003/0060674 A1 | 3/2003 | Gifford, III et al. |
| 2003/0065248 A1 | 4/2003 | Lau et al. |
| 2003/0069467 A1 | 4/2003 | Lau et al. |
| 2003/0078465 A1 | 4/2003 | Pai et al. |
| 2003/0078653 A1 | 4/2003 | Vesely et al. |
| 2003/0078671 A1 | 4/2003 | Lesniak et al. |
| 2003/0105519 A1 | 6/2003 | Fasol et al. |
| 2003/0120340 A1 | 6/2003 | Liska et al. |
| 2003/0130730 A1 | 7/2003 | Cohn et al. |
| 2003/0130731 A1 | 7/2003 | Vidlund et al. |
| 2003/0144697 A1 | 7/2003 | Mathis et al. |
| 2003/0149333 A1 | 8/2003 | Alferness |
| 2003/0153946 A1 | 8/2003 | Kimblad |
| 2003/0158570 A1 | 8/2003 | Ferrazzi |
| 2003/0166992 A1 | 9/2003 | Schweich, Jr. et al. |
| 2003/0171641 A1 | 9/2003 | Schweich, Jr. et al. |
| 2003/0171776 A1 | 9/2003 | Adams et al. |
| 2003/0171806 A1 | 9/2003 | Mathis et al. |
| 2003/0181928 A1 | 9/2003 | Vidlund et al. |
| 2003/0191538 A1 | 10/2003 | Buckberg et al. |
| 2003/0199733 A1 | 10/2003 | Shapland et al. |
| 2003/0212453 A1 | 11/2003 | Mathis et al. |
| 2003/0225454 A1 | 12/2003 | Mathis et al. |
| 2003/0229260 A1 | 12/2003 | Girard et al. |
| 2003/0229261 A1 | 12/2003 | Girard et al. |
| 2003/0229265 A1 | 12/2003 | Girard et al. |
| 2003/0229266 A1 | 12/2003 | Cox et al. |
| 2003/0233022 A1 | 12/2003 | Vidlund et al. |
| 2003/0233142 A1 | 12/2003 | Morales et al. |
| 2003/0236569 A1 | 12/2003 | Mathis et al. |
| 2004/0002719 A1 | 1/2004 | Oz et al. |
| 2004/0003819 A1 | 1/2004 | St. Goar et al. |
| 2004/0010305 A1 | 1/2004 | Alferness et al. |
| 2004/0015039 A1 | 1/2004 | Melvin |
| 2004/0015040 A1 | 1/2004 | Melvin |
| 2004/0015041 A1 | 1/2004 | Melvin |
| 2004/0019377 A1 | 1/2004 | Taylor et al. |
| 2004/0019378 A1 | 1/2004 | Hlavka et al. |
| 2004/0024286 A1 | 2/2004 | Melvin |
| 2004/0030382 A1 | 2/2004 | St. Goar et al. |
| 2004/0034271 A1 | 2/2004 | Melvin et al. |
| 2004/0039442 A1 | 2/2004 | St. Goar et al. |
| 2004/0039443 A1 | 2/2004 | Solem et al. |
| 2004/0044365 A1 | 3/2004 | Bachman |
| 2004/0049115 A1 | 3/2004 | Murphy et al. |
| 2004/0049116 A1 | 3/2004 | Murphy et al. |
| 2004/0059180 A1 | 3/2004 | Melvin |
| 2004/0059181 A1 | 3/2004 | Alferness |
| 2004/0059182 A1 | 3/2004 | Alferness |
| 2004/0059187 A1 | 3/2004 | Alferness |
| 2004/0059188 A1 | 3/2004 | Alferness |
| 2004/0059189 A1 | 3/2004 | Alferness |
| 2004/0059351 A1 | 3/2004 | Eigler et al. |
| 2004/0064014 A1 | 4/2004 | Melvin et al. |
| 2004/0073302 A1 | 4/2004 | Rourke et al. |
| 2004/0092962 A1 | 5/2004 | Thornton et al. |
| 2004/0093023 A1 | 5/2004 | Allen et al. |
| 2004/0098116 A1 | 5/2004 | Callas et al. |
| 2004/0102678 A1 | 5/2004 | Haindl |
| 2004/0102679 A1 | 5/2004 | Alferness et al. |
| 2004/0102839 A1 | 5/2004 | Cohn et al. |
| 2004/0102840 A1 | 5/2004 | Solem et al. |
| 2004/0111095 A1 | 6/2004 | Gordon et al. |
| 2004/0111101 A1 | 6/2004 | Chin |
| 2004/0122448 A1 | 6/2004 | Levine |
| 2004/0122512 A1 | 6/2004 | Navia et al. |
| 2004/0122513 A1 | 6/2004 | Navia et al. |
| 2004/0127980 A1 | 7/2004 | Kowalsky et al. |
| 2004/0127981 A1 | 7/2004 | Rahdert et al. |
| 2004/0127982 A1 | 7/2004 | Machold et al. |
| 2004/0127983 A1 | 7/2004 | Mortier et al. |
| 2004/0133062 A1 | 7/2004 | Pai et al. |
| 2004/0133063 A1 | 7/2004 | McCarthy et al. |
| 2004/0133069 A1 | 7/2004 | Shapland et al. |
| 2004/0133220 A1 | 7/2004 | Lashinski et al. |
| 2004/0133240 A1 | 7/2004 | Adams et al. |
| 2004/0133273 A1 | 7/2004 | Cox |
| 2004/0138526 A1 | 7/2004 | Guenst |
| 2004/0138744 A1 | 7/2004 | Lashinski et al. |
| 2004/0143323 A1 | 7/2004 | Chawla |
| 2004/0148019 A1 | 7/2004 | Vidlund et al. |
| 2004/0148020 A1 | 7/2004 | Vidlund et al. |
| 2004/0152947 A1 | 8/2004 | Schroeder et al. |
| 2004/0158123 A1 | 8/2004 | Jayaraman |
| 2004/0158321 A1 | 8/2004 | Reuter |
| 2004/0162610 A1 | 8/2004 | Liska et al. |
| 2004/0167374 A1 | 8/2004 | Schweich et al. |
| 2004/0167539 A1 | 8/2004 | Kuehn et al. |
| 2004/0171907 A1 | 9/2004 | Alferness et al. |
| 2004/0171908 A1 | 9/2004 | Alferness et al. |
| 2004/0171909 A1 | 9/2004 | Alferness |
| 2004/0172046 A1 | 9/2004 | Hlavka et al. |
| 2004/0176678 A1 | 9/2004 | Murphy et al. |
| 2004/0176679 A1 | 9/2004 | Murphy et al. |
| 2004/0176840 A1 | 9/2004 | Langberg et al. |

| | | |
|---|---|---|
| 2004/0181121 A1 | 9/2004 | Alferness et al. |
| 2004/0181122 A1 | 9/2004 | Alferness et al. |
| 2004/0181123 A1 | 9/2004 | Alferness et al. |
| 2004/0181124 A1 | 9/2004 | Alferness |
| 2004/0181125 A1 | 9/2004 | Alferness et al. |
| 2004/0181126 A1 | 9/2004 | Buckberg et al. |
| 2004/0181238 A1 | 9/2004 | Zarbatany et al. |
| 2004/0186342 A1 | 9/2004 | Vanden Hock et al. |
| 2004/0186566 A1 | 9/2004 | Hindrichs et al. |
| 2004/0193191 A1 | 9/2004 | Starksen et al. |
| 2004/0193260 A1 | 9/2004 | Alferness et al. |
| 2004/0199183 A1 | 10/2004 | Oz et al. |
| 2004/0206363 A1 | 10/2004 | McCarthy et al. |
| 2004/0210240 A1 | 10/2004 | Saint |
| 2004/0210303 A1 | 10/2004 | Sedransk |
| 2004/0210304 A1 | 10/2004 | Seguin et al. |
| 2004/0210306 A1 | 10/2004 | Quijano et al. |
| 2004/0210307 A1 | 10/2004 | Khairkhahan |
| 2004/0220593 A1 | 11/2004 | Greenhalgh |
| 2004/0225300 A1 | 11/2004 | Goldfarb et al. |
| 2004/0243227 A1 | 12/2004 | Starlksen et al. |
| 2004/0243228 A1 | 12/2004 | Kowalsky et al. |
| 2004/0243229 A1 | 12/2004 | Vidlund et al. |
| 2004/0249452 A1 | 12/2004 | Adams et al. |
| 2004/0254600 A1 | 12/2004 | Zarbatany et al. |
| 2004/0260317 A1 | 12/2004 | Bloom et al. |
| 2004/0260393 A1 | 12/2004 | Rahdert et al. |
| 2004/0267083 A1 | 12/2004 | McCarthy et al. |
| 2004/0267329 A1 | 12/2004 | Raman et al. |
| 2004/0267358 A1 | 12/2004 | Reitan |
| 2005/0004428 A1 | 1/2005 | Cox et al. |
| 2005/0004665 A1 | 1/2005 | Aklog |
| 2005/0004666 A1 | 1/2005 | Alfieri et al. |
| 2005/0004667 A1 | 1/2005 | Swinford et al. |
| 2005/0004668 A1 | 1/2005 | Aklog et al. |
| 2005/0010240 A1 | 1/2005 | Mathis et al. |
| 2005/0010283 A1 | 1/2005 | Vijay |
| 2005/0010286 A1 | 1/2005 | Vijay |
| 2005/0021056 A1 | 1/2005 | St. Goar et al. |
| 2005/0021057 A1 | 1/2005 | St. Goar et al. |
| 2005/0021121 A1 | 1/2005 | Reuter et al. |
| 2005/0021135 A1 | 1/2005 | Ryan et al. |
| 2005/0027351 A1 | 2/2005 | Reuter et al. |
| 2005/0027353 A1 | 2/2005 | Alferness et al. |
| 2005/0027369 A1 | 2/2005 | Eldridge et al. |
| 2005/0033419 A1 | 2/2005 | Alferness et al. |
| 2005/0033446 A1 | 2/2005 | Deem et al. |
| 2005/0038506 A1 | 2/2005 | Webler et al. |
| 2005/0038507 A1 | 2/2005 | Alferness et al. |
| 2005/0038509 A1 | 2/2005 | Ashe |
| 2005/0043792 A1 | 2/2005 | Solem et al. |
| 2005/0049679 A1 | 3/2005 | Taylor et al. |
| 2005/0049698 A1 | 3/2005 | Bolling et al. |
| 2005/0055087 A1 | 3/2005 | Starksen |
| 2005/0055089 A1 | 3/2005 | Macoviak et al. |
| 2005/0059854 A1 | 3/2005 | Vanden Hoek et al. |
| 2005/0060030 A1 | 3/2005 | Lashinski et al. |
| 2005/0065550 A1 | 3/2005 | Starlsen et al. |
| 2005/0065598 A1 | 3/2005 | Mathis et al. |
| 2005/0065601 A1 | 3/2005 | Lee et al. |
| 2005/0070998 A1 | 3/2005 | Rourke et al. |
| 2005/0071000 A1 | 3/2005 | Liddicoat et al. |
| 2005/0075723 A1 | 4/2005 | Schroeder et al. |
| 2005/0075727 A1 | 4/2005 | Wheatley |
| 2005/0080402 A1 | 4/2005 | Santamore et al. |
| 2005/0080483 A1 | 4/2005 | Solem et al. |
| 2005/0085688 A1 | 4/2005 | Girard et al. |
| 2005/0095268 A1 | 5/2005 | Walsh et al. |
| 2005/0096666 A1 | 5/2005 | Gordon et al. |
| 2005/0096740 A1 | 5/2005 | Langberg et al. |
| 2005/0107810 A1 | 5/2005 | Morales et al. |
| 2005/0107811 A1 | 5/2005 | Starksen et al. |
| 2005/0107812 A1 | 5/2005 | Starksen et al. |
| 2005/0113635 A1 | 5/2005 | Whayne et al. |
| 2005/0113811 A1 | 5/2005 | Houser et al. |
| 2005/0119519 A9 | 6/2005 | Girard et al. |
| 2005/0131533 A1 | 6/2005 | Alfier et al. |
| 2005/0137449 A1 | 6/2005 | Nieminen et al. |
| 2005/0137450 A1 | 6/2005 | Aronson et al. |
| 2005/0137451 A1 | 6/2005 | Gordon et al. |
| 2005/0137685 A1 | 6/2005 | Nieminen et al. |
| 2005/0137700 A1 | 6/2005 | Spence et al. |
| 2005/0143811 A1 | 6/2005 | Realyvasquez |
| 2005/0149179 A1 | 7/2005 | Mathis et al. |
| 2005/0149180 A1 | 7/2005 | Mathis et al. |
| 2005/0149182 A1 | 7/2005 | Alferness et al. |
| 2005/0159810 A1 | 7/2005 | Filsoufi |
| 2005/0177228 A1 | 8/2005 | Solem et al. |
| 2005/0184122 A1 | 8/2005 | Hlavka et al. |
| 2005/0187619 A1 | 8/2005 | Mathis et al. |
| 2005/0192474 A1 | 9/2005 | Vanden Hoek et al. |
| 2005/0192666 A1 | 9/2005 | McCarthy |
| 2005/0197527 A1 | 9/2005 | Bolling |
| 2005/0197528 A1 | 9/2005 | Vanden Hoek et al. |
| 2005/0197692 A1 | 9/2005 | Pai et al. |
| 2005/0197693 A1 | 9/2005 | Pai et al. |
| 2005/0209690 A1 | 9/2005 | Mathis et al. |
| 2005/0216039 A1 | 9/2005 | Lederman |
| 2005/0216077 A1 | 9/2005 | Mathis et al. |
| 2005/0216078 A1 | 9/2005 | Starksen et al. |
| 2005/0222488 A1 | 10/2005 | Chang et al. |
| 2005/0222489 A1 | 10/2005 | Rahdert et al. |
| 2005/0222678 A1 | 10/2005 | Lashinski et al. |
| 2005/0228217 A1 | 10/2005 | Alferness et al. |
| 2005/0228422 A1 | 10/2005 | Machold et al. |
| 2005/0240200 A1 | 10/2005 | Bergheim |
| 2005/0246014 A1 | 11/2005 | McCarthy |
| 2005/0256567 A1 | 11/2005 | Lim et al. |
| 2005/0256568 A1 | 11/2005 | Lim et al. |
| 2005/0256569 A1 | 11/2005 | Lim et al. |
| 2005/0261704 A1 | 11/2005 | Mathis et al. |
| 2005/0267574 A1 | 12/2005 | Cohn et al. |
| 2005/0272969 A1 | 12/2005 | Alferness et al. |
| 2005/0278022 A1 | 12/2005 | Lim |
| 2006/0004443 A1 | 1/2006 | Liddicoat et al. |
| 2006/0009842 A1 | 1/2006 | Huynh et al. |
| 2006/0030885 A1 | 2/2006 | Hyde |
| 2006/0036317 A1 | 2/2006 | Vidlund et al. |
| 2006/0041306 A1 | 2/2006 | Vidlund et al. |
| 2006/0052868 A1 | 3/2006 | Mortier et al. |
| 2006/0100699 A1 | 5/2006 | Vidlund et al. |
| 2006/0161040 A1 | 7/2006 | McCarthy et al. |
| 2006/0195012 A1 | 8/2006 | Mortier et al. |
| 2007/0004962 A1 | 1/2007 | Alferness et al. |
| 2007/0112244 A1 | 5/2007 | McCarthy et al. |
| 2007/0225547 A1 | 9/2007 | Alferness |

FOREIGN PATENT DOCUMENTS

| | | |
|---|---|---|
| DE | 36 14 292 C1 | 11/1987 |
| DE | 42 34 127 A1 | 5/1994 |
| DE | 295 00 381 U1 | 7/1995 |
| DE | 296 18 925 U1 * | 1/1997 |
| DE | 296 19 294 U1 | 8/1997 |
| DE | 298 24 017 U1 | 6/1998 |
| DE | 198 26 675 A1 | 3/1999 |
| DE | 199 47 885 A1 | 4/2000 |
| EP | 0 583 012 A1 | 2/1994 |
| EP | 0 792 621 A1 | 9/1997 |
| EP | 0 820 729 A1 | 1/1998 |
| EP | 1 129 736 A1 | 9/2001 |
| GB | 2214428 | 9/1989 |
| NL | 9 200 878 | 12/1993 |
| SU | 1335260 A1 * | 2/1989 |
| WO | WO 91/19465 A1 | 12/1991 |
| WO | WO 95/06447 A1 | 3/1995 |
| WO | WO 95/16407 A1 | 6/1995 |
| WO | WO 95/16476 A1 | 6/1995 |
| WO | WO 96/02197 A1 | 2/1996 |
| WO | WO 96/04852 A1 | 2/1996 |
| WO | WO 96/40356 A1 | 12/1996 |
| WO | WO 97/14286 A2 | 4/1997 |
| WO | WO 97/24082 A1 | 7/1997 |
| WO | WO 97/24083 A1 | 7/1997 |
| WO | WO 97/24101 A1 | 7/1997 |
| WO | WO 97/41779 | 11/1997 |
| WO | WO 98/03213 A1 | 1/1998 |
| WO | WO 98/14136 A1 | 4/1998 |
| WO | WO 98/17347 A1 | 4/1998 |

| | | | |
|---|---|---|---|
| WO | WO 98/18393 A1 | 5/1998 | |
| WO | WO 98/26738 A1 | 6/1998 | |
| WO | WO 98/29041 A1 | 7/1998 | |
| WO | WO 98/32382 A1 | 7/1998 | |
| WO | WO 98/44969 A1 | 10/1998 | |
| WO | WO 98/58598 A1 | 12/1998 | |
| WO | WO 99/00059 A1 | 1/1999 | |
| WO | WO 99/11201 A2 | 3/1999 | |
| WO | WO 99/13777 A1 | 3/1999 | |
| WO | WO 99/13936 | 3/1999 | |
| WO | WO 99/16350 | 4/1999 | |
| WO | WO 99/22784 A1 | 5/1999 | |
| WO | WO 99/30647 A1 | 6/1999 | |
| WO | WO 99/44534 A1 | 9/1999 | |
| WO | WO 99/44680 A1 | 9/1999 | |
| WO | WO 99/52470 A1 | 10/1999 | |
| WO | WO 99/53977 A1 | 10/1999 | |
| WO | WO 99/56655 A1 | 11/1999 | |
| WO | WO 99/62727 | 12/1999 | |
| WO | WO 99/66969 A1 | 12/1999 | |
| WO | WO 00/02500 A1 | 1/2000 | |
| WO | WO 00/03759 A2 | 1/2000 | |
| WO | WO 00/06026 A2 | 2/2000 | |
| WO | WO 00/06028 A1 | 2/2000 | |
| WO | WO 00/13722 A1 | 3/2000 | |
| WO | WO 00/18320 A1 | 4/2000 | |
| WO | WO 00/25842 A1 | 5/2000 | |
| WO | WO 00/25853 A2 | 5/2000 | |
| WO | WO 00/27304 A1 | 5/2000 | |
| WO | WO 00/28912 A1 | 5/2000 | |
| WO | WO 00/28918 A1 | 5/2000 | |
| WO | WO 00/36995 A2 | 6/2000 | |
| WO | WO 00/42919 A1 | 7/2000 | |
| WO | WO 00/42950 A2 | 7/2000 | |
| WO | WO 00/42951 A1 | 7/2000 | |
| WO | WO 00/45735 | 8/2000 | |
| WO | WO 00/60995 A2 | 10/2000 | |
| WO | WO 00/61033 A1 | 10/2000 | |
| WO | WO 00/62715 A1 | 10/2000 | |
| WO | WO 01/00111 A1 | 1/2001 | |
| WO | WO 01/03608 A1 | 1/2001 | |
| WO | WO 01/19291 A1 | 3/2001 | |
| WO | WO 01/19292 A1 | 3/2001 | |
| WO | WO 01/21070 A1 | 3/2001 | |
| WO | WO 01/21098 A1 | 3/2001 | |
| WO | WO 01/21099 A1 | 3/2001 | |
| WO | WO 01/21247 A1 | 3/2001 | |
| WO | WO 01/54562 A1 | 3/2001 | |
| WO | WO 01/95832 A1 | 3/2001 | |
| WO | WO 01/26557 A1 | 4/2001 | |
| WO | WO 01/28432 A1 | 4/2001 | |
| WO | WO 01/49217 A2 | 7/2001 | |
| WO | WO 01/50981 A1 | 7/2001 | |
| WO | WO 01/54618 A1 | 8/2001 | |
| WO | WO 01/54745 A2 | 8/2001 | |
| WO | WO 01/67985 A1 | 9/2001 | |
| WO | WO 01/70116 A1 | 9/2001 | |
| WO | WO 01/78625 A1 | 10/2001 | |
| WO | WO 01/85061 A2 | 11/2001 | |
| WO | WO 01/91667 A2 | 12/2001 | |
| WO | WO 01/95830 A2 | 12/2001 | |
| WO | WO 01/95831 A2 | 12/2001 | |
| WO | WO 02/11625 A2 | 2/2002 | |
| WO | WO 02/13726 A2 | 2/2002 | |
| WO | WO 02/19917 A1 | 3/2002 | |
| WO | WO 02/28450 A2 | 4/2002 | |
| WO | WO 02/30292 A1 | 4/2002 | |
| WO | WO 02/30335 A2 | 4/2002 | |
| WO | WO 02/34167 A2 | 5/2002 | |
| WO | WO 02/38081 A2 | 5/2002 | |
| WO | WO 02/43617 A2 | 6/2002 | |
| WO | WO 02/053206 A2 | 7/2002 | |
| WO | WO 02/060352 A1 | 8/2002 | |
| WO | WO 02/062263 A2 | 8/2002 | |
| WO | WO 02/062270 A1 | 8/2002 | |
| WO | WO 02/062408 A2 | 8/2002 | |
| WO | WO 02/064035 A1 | 8/2002 | |
| WO | WO 02/076284 A2 | 10/2002 | |
| WO | WO 02/078576 A2 | 10/2002 | |
| WO | WO 02/085251 A1 | 10/2002 | |
| WO | WO 02/096275 A2 | 12/2002 | |
| WO | WO 03/001893 A2 | 1/2003 | |
| WO | WO 03/007778 A2 | 1/2003 | |
| WO | WO 03/015611 A2 | 2/2003 | |
| WO | WO 03/022131 A2 | 3/2003 | |
| WO | WO 03/059209 A2 | 7/2003 | |

OTHER PUBLICATIONS

McGoon, M.D. et al., "Correction of the univentricular heart having two atrioventricular valves," *The Journal of Thoracic and Cardiovascular Surgery*, Aug. 1977, pp. 218-226, vol. 74, No. 2, Mosby-Year Book, Inc.

Lev, M.D., et al., "Single (Primitive) Ventricle," *Circulation*, May 1969, pp. 577-591, vol. 39, American Heart Association.

Westaby With Bosher, "Landmarks in Cardiac Surgery," *Surgery for Coronary Artery Disease*, 1997, pp. 198-199, Isis Medical Media Ltd., Oxford, United Kingdom.

Shumacker, "Cardiac Aneurysms," *The Evolution of Cardiac Surgery*, 1992, pp. 159-165, Indiana University Press, Bloomington, IN.

Feldt, M.D., "Current status of the septation procedure for univentricular heart," *The Journal of Thoracic and Cardiovascular Surgery*, Jul. 1981, pp. 93-97, vol. 82, No. 1, The C.V. Mosby Co.

Doty, M.D., "Septation of the univentricular heart," *The Journal of Thoracic and Cardiovascular Surgery*, Sep. 1979, pp. 423-430, vol. 78, No. 3, The C.V. Mosby Co.

Carpentier et al., "Myocardial Substitution with a Stimulated Skeletal Muscle: First Successful Clinical Case," Letter to the Editor, *The Lancet*, p. 1267, Sep. 25, 1996, Elsevier Science, Ltd.

Ianuzzo et al., "Preservation of the Latissimus Dorsi Muscle During Cardiomyoplasty Surgery," *J. Card. Surg.*, 1996:11:99-108, Wiley Periodicals, Inc.

Ianuzzo et al., "On Preconditioning of Skeletal Muscle: Application to Dynamic Cardiomyoplasty," Invited Commentary, *J. Card. Surg.*, 1996:11:109-110, Wiley Periodicals, Inc.

Moreira et al., "Latissimus Dorsi Cardiomyoplasty in the Treatment of Patients with Dilated Cardiomyopathy," *Circulation*, Supplement IV, 1990, pp. 257-263, American Heart Association.

Lucas et al., "Long-Term Follow-Up (12 to 35 Weeks) After Dynamic Cardiomyoplasty," *JACC*, vol. 22, No. 3, Sep. 1993:758-67, American College of Cardiology.

Batista et al., "Partial Left Ventriculectomy to Improve Left Ventricular Function in End-Stage Heart Disease," *J. Card. Surg.*, 1996:11:96-98, Wiley Periodicals, Inc.

"Congestive Heart Failure in the United States: A New Epidemic" Data Fact Sheet, National Heart, Lung, and Blood Institute, Dec. 9, 1996, pp. 1-6, National Institutes of Health.

Kormos et al., "Experience with Univentricular Support in Mortally III Cardiac Transplant Candidates," *Ann. Thorac. Surg.*, 1990:49:261-71, Elsevier, The Netherlands.

Wampler et al., "Treatment of Cardiogenic Shock with the Hemopump Left Ventricular Assist Device," *Ann. Thorac. Surg.*, 1991:52:506-13, Elsevier, The Netherlands.

Burnett et al., "Improved Survival After Hemopump Insertion in Patients Experiencing Postcardiotomy Cardiogenic Shock During Cardiopulmonary Bypass," From the Section of Transplantation, Division of Cardiovascular Surgery, Texas Heart Institute and St. Luke's Episcopal Hospital, Houston, Texas, Jul.-Sep. 1990, vol. 36, No. 3, pp. 626-628, J. B. Lippincott Company.

Phillips et al., "Hemopump Support for the Failing Heart," From the Department of Cardiovascular Medicine and Surgery, Mercy Hospital Medical Center, Des Moines, Iowa, Jul.-Sep. 1990, vol. 36, No. 3, pp. 629-631, J. B. Lippincott Company.

Deeb et al., "Clinical Experience with the Nimbus Pump," From the University of Michigan Medical Center Section of Thoracic Surgery and Division of Cardiology, Ann Arbor, Michigan, Jul.-Sep. 1990, vol. 36, No. 3, pp. 632-636, J. B. Lippincott Company.

Bearnson et al., "Development of a Prototype Magnetically Suspended Rotor Ventricular Assist Device," *ASAIO Journal*, Jul.-Aug. 1996, vol. 42, No. 4, pp. 275-280, Lippincott-Raven Publishers.

Sakakibara et al., "A Muscle Powered Cardiac Assist Device for Right Ventricular Support: Total Assist or Partial Assist?," *Trans.*

Am.Soc. Artif. Intern. Organs, Jul.-Sep. 1990, vol. 36, No. 3, pp. 372-375, J. B. Lippincott Company.

Medtronic, Inc. 1996 Annual Shareholders Report, 79 pages, Medtronic, Inc.

Abiomed, Inc. Annual Report 1996, 32 pages, Abiomed, Inc.

Press Release dated Sep. 16, 1996, "Abiomed Wins $8.5 Million Federal Contract to Qualify its Artificial Heart for Human Trials," 5 pages, Abiomed, Inc.

Press Release dated Sep. 26, 1996, Abiomed's Temporary Artificial Heart System Reaches 200 U.S. Medical Center Milestone, 1 page, Abiomed, Inc.

Press Release dated May 17, 1996, "Abiomed Receives FDA Approval to Expand Indications for Use of Cardiac Assist System," 1 page, Abiomed, Inc.

Press Release dated Oct. 3, 1995, "Abiomed Wins $4.35 Million Contract from the National Heart, Lung and Blood Institutes to Develop Implantable Heart Booster," 1 page, Abiomed, Inc.

Press Release dated Sep. 29, 1995, "Abiomed" Wins NIH Grant to Develop Calcification-Resistant Plastic Heart Valve, 1 page, Abiomed, Inc.

Press Release dated Aug. 25, 1995, "Abiomed Wins Research Grant from NIH to Develop Suturing Instrument for Abdominal surgery," 1 page, Abiomed, Inc.

Press Release dated Aug. 11, 1995, "Abiomed Receives Grant from NIH to Develop Disposable Bearingless Centrifugal Blood Pump," 1 page, Abiomed, Inc.

Press Release dated Jun. 9, 1995, "Abiomed Receives Grant from National Institutes of Health to Develop a Laser Welding Technique for Tissue Repair," 1 page, Abiomed, Inc.

Press Release dated Apr. 27, 1995, "Abiomed's Temporary Artificial Heart System Reaches 1,000 Patient Milestone; BVS-5000 in More Than 100 U.S. Medical Centers," 1 page, Abiomed, Inc.

"Reversible Cardiomyopathy," *Thoratec's Heartbeat*, vol. 10.2, Aug. 1996, 4 pages, Thoratec Laboratories Corporation.

Tsai et al., "Surface Modifying Additives for Improved Device-Blood Compatibility," *ASAIO Journal*, 1994, pp. 619-624, J. B. Lippincott Company.

Farrar et al., "A New Skeletal Muscle Linear-Pull Energy Convertor as a Power Source for Prosthetic Support Devices," *The Journal of Heart & Lung Transplantation*, vol. 11, No. 5, Sep. 1992, pp. 341-349, Elsevier, The Netherlands.

Brochure entitled "Thoratec Ventricular Assist Device System—Because Heart Patients Come in All Sizes," date even with or prior to Jan. 2, 1997, 5 pages, Thoratec Laboratories Corporation.

Press Release dated Oct. 3, 1994, "Heartmate System Becomes First Implantable Cardiac-Assist Device to be Approved for Commercial Sale in the U.S.," 2 pages, Thermo Cardiosystems, Inc.

Bocchi et al., "Clinical Outcome after Surgical Remodeling of Left Ventricle in Candidates to Heart Transplantation with Idiopathic Dilated Cardiomypathy—Short Term Results," Supplement to *Circulation*, supp. II, vol. 96, No. 9, Nov. 4, 1997, 1 page, American Heart Association.

Bach et al., "Early Improvement in Congestive Heart Failure after Correction of Secondary Mitral Regurgitation in End-Stage Cardiomyopathy" *American Heart Journal*, Jun. 1995, pp. 1165-1170, Mosby-Year Book, Inc.

Schuler et al., "Temporal Response of Left Ventricular Performance to Mitral Valve Surgery," *Circulation*, vol. 59, No. 6, Jun. 1979, pp. 1218-1231, American Heart Association.

Huikuri, "Effect of Mitral Valve Replacement on Left Ventricular Function in Mitral Regurgitation," *Br. Heart J.*, vol. 49, 1983, pp. 328-333, British Medical Journal Group.

Pitarys II et al., "Long-Term Effects of Excision of the Mitral Apparatus on Global and Regional Ventricular Function in Humans," *JACC*, vol. 15, No. 3, Mar. 1, 1990, pp. 557-563, American College of Cardiology.

Bolling et al., "Surgery for Acquired Heart Disease/Early Outcome of Mitral Valve Reconstruction in Patients with End-Stage Cardiomyopathy," *The Journal of Thoracic and Cardiovascular Surgery*, vol. 109, No. 4, Apr. 1995, pp. 676-683, Mosby-Year Book, Inc.

Masahiro et al., "Surgery for Acquired Heart Disease/Effects of Preserving Mitral Apparatus on Ventricular Systolic Function in Mitral Valve Operations in Dogs," *The Journal of Thoracic and Cardiovascular Surgery*, vol. 106, No. 6, Dec. 1993, pp. 1138-1146, Mosby-Year Book, Inc.

Dickstein et al., "Heart Reduction Surgery: An Analysis of the Impact on Cardiac Function," *The Journal of Thoracic and Cardiovascular Surgery*, vol. 113, No. 6, Jun. 1997, 9 pages, Mosby-Year Book, Inc.

McCarthy et al., "Early Results with Partial Left Ventriculectomy," From the Departments of Thoracic and Cardiovascular Surgery, Cardiology, and Transplant Center, Cleveland Clinic Foundation, Presented at the 77th Annual Meeting of the American Association of Thoracic Surgeons, May 1997, 33 pages.

Alonso-Lej, M.D., "Adjustable Annuloplasty for Tricuspid Insufficiency," *The Annals of Thoracic Surgery*, vol. 46, No. 3, Sep. 1988, 2 pages, Elsevier, The Netherlands.

Kurlansky et al., "Adjustable Annuloplasty for Tricuspid Insufficiency," *Ann. Thorac. Surg.*, 44:404-406, Oct. 1987, Elsevier, The Netherlands.

Savage, M.D., "Repair of left ventricular aneurysm," *The Journal of Thoracic and Cardiovascular Surgery*, vol. 104, No. 3, Sep. 1992, pp. 752-762, Mosby-Year Book, Inc., St. Louis, MO.

Melvin, "Ventricular Radius Reduction Without Resection: A Computational Analysis," *ASAIO Journal*, 45:160-165, 1999, Lippincott-Raven Publishers.

Cox, "Left Ventricular Aneurysms: Pathophysiologic Observations and Standard Resection," *Seminars in Thoracic and Cardiovascular Surgery*, vol. 9, No. 2, Apr. 1997, pp. 113-122, W. B. Sanders Company.

Boyd et al., "Tricuspid Annuloplasty," *The Journal of Thoracic and Cardiovascular Surgery*, vol. 68, No. 3, Sep. 1974, 8 pages, Mosby-Year Book, Inc.

Kay et al., "Surgical Treatment of Mitral Insufficiency", *The Journal of Thoracic Surgery*, 1955, 29:618-620, The C. V. Mosby Company, St. Louis, MO.

Harken et al., "The Surgical Correction of Mitral Insufficiency", *The Journal of Thoracic Surgery*, 1954, 28:604-627, The C. V. Mosby Company, St. Louis, MO.

Bailey et al., "Closed Intracardiac Tactile Surgery", *Diseases of the Chest*, 1952, XXII:1-24, American College of Chest Physicians.

Sakakibara, "A Surgical Approach to the Correction of Mitral Insufficiency", *Annals of Surgery*, 1955, 142:196-203, J.B. Lippincott Company.

Glenn et al., "The Surgical Treatment of Mitral Insufficiency: The Fate of a Vascularized Transchamber Intracardiac Graft", *Annals of Surgery*, Apr. 1955, 141:4:510-518 J.B. Lippincott Company.

Kay et al., "Surgical Treatment of Mitral Insufficiency", *Surgery*, May 1955, 37:5:697-706, The C. V. Mosby Company, St. Louis, MO.

Bailey et al., "The Surgical Correction of Mitral Insufficiency by the Use of Pericardial Grafts", *The Journal of Thoracic Surgery*, Dec. 1954, 28:6:551-603, The C. V. Mosby Company, St. Louis, MO.

Harken et al., "The Surgical Correction of Mitral Insufficency", *Surgical Forum*, Oct. 1953, 4:4-7, W. B. Saunders Company.

Shumacker, Jr., "Attempts to Control Mitral Regurgitation", *The Evolution of Cardiac Surgery*, Aug. 1, 1992, 203-210, Indiana University Press.

Batista, MD et al., "Partial Left Ventriculectomy to Treat End-Stage Heart Disease", *Ann. Thorac. Surg.*, 64:634-8, 1997, Elsevier Science, Inc., The Netherlands.

Melvin DB et al., Reduction of Ventricular Wall Tensile Stress by Geometric Remodeling Device, *Poster text, ASAIO* 1999, Lippincott-Raven Publishers, 6 pages.

Hayden et al., "Scintiphotographic Studies of Acquired Cardiovascular Disease," *Seminars in Nuclear Medicine*, vol. III, No. 2, Apr. 1973, pp. 177-190, Grune & Stratton, Inc.

McCarthy, Transcription of Mar. 13, 2000, presentation given at ACC, pp . 1-9.

"Acorn Cardiovascular Abstracts", Nov. 13, 2000, acorn cardiovascular, inc., 6 pages.

Nation's First "Heart Jacket" Surgery to Treat Heart Failure Performed at HUP: Novel "Cardiac Support Device" Comes to America After Promising Results in Europe, Jun. 26, 2000, www.devicelink.com, pp. 1-3.

Acorn Cardiovascular Company Overview, Jun. 2000, acorn cardiovascular, inc., 6 pages.

Acorn Cardiovascular Business Plan, Executive Summary, May 2000, acorn cardiovascular, inc., pp. 1-7.
"Acorn Cardiovascular Highlights Abstracts", Mar. 10, 1999, acorn cardiovascular, inc., 1 page.
"Acorn Cardiovascular Highlights Abstracts", Apr. 19, 1999, acorn cardiovascular, inc., 1 page.
"Acorn Cardiovascular Highlights Abstracts", Oct. 1-2, 1999, acorn cardiovascular, inc., 1 page.
"Acorn Cardiovascular Highlights Abstracts", Nov. 9, 1999, acorn cardiovascular, inc., 1 page.
Baim, MD, Brigham and Women's Hospital, Harvard Medical School, *Percutaneous Treatment of Mitral Regurgitation*, 2005, 19 pages.
Dullum, Mercedes K.C., *Update on Restraint Devices for Congestive Heart Failure*, Abstract and presentation slides given at Tech-Con 2005 for Society of Thoracic Surgeons, Jan. 23, 2005, 11 pages.
"Heart 'jacket' could help stop heart failure progress," *Clinica*, Jul. 10, 2000, PJB Publications, 1 page.
McCarthy et al., "Device Based Left Ventricular Shape Change Immediately Reduces Left Ventricular Volume and Increases Ejection Fraction in a Pacing Induced Cardiomyopathy Model in Dogs: A Pilot Study," JACC, Feb. 2000, Elsevier Science, Inc., The Netherlands, 1 page.

Alonso-Lej, *The Journal of Thoracic and Cardiovascular Surgery*, vol. 68, No. 3, Sep. 1974, p. 349, Elsevier, The Netherlands.
Chachques et al., "Latissimus Dorsi Dynamic Cardiomyoplasty," *Ann. Thorac. Surg.*, 1989:47:600-604.
Timek, Thomasz A., MD, et al, The Journal of Thoracic Surgery, vol. 123, No. 5, Surgery for Acquired Cardiovascular Disease, *Septal-lateral annular cinching abolishes acute ischemic mitrel regurgitation*, pp. 881-888, 2002.
Timek, Thomasz A. et al, Department of Cardiothoracic Surgery and Division of Cardiovascular Medicine, Stanford University School of Medicine, Stanford, CA, *Septal-Lateral Annular Cinching ('SLAC') reduces Mitral Annular Size without Perturbing Normal Annular Dynamics*, 2002, pp. 2-10, J. Heart Valve Dis . (11) 1.
McCarthy et al., "Clinical Experience with the Novacor Ventricular Assist System," *J. Thorac. Cardiovasc. Surg.*, 1991:102-578-87.
Hung, MD et al., "Reverse Ventricular Remodeling Reduces Ischemic Mitral Regurgitation," *Circulation*,2002, pp. 2594-2600, vol. 106.
US 6,197,052, 03/2001, Cosgrove et al. (withdrawn)

* cited by examiner

VALVE TO MYOCARDIUM TENSION MEMBERS DEVICE AND METHOD

CROSS-REFERENCE TO RELATED APPLICATIONS

This is a continuation of application Ser. No. 09/981,790, filed Oct. 19, 2001, now pending, which is a continuation of application Ser. No. 08/992,316, filed Dec. 17, 1997, now U.S. Pat. No. 6,332,893, both of which are incorporated herein by reference.

BACKGROUND OF THE INVENTION

The present invention pertains generally to the field of heart valve repair. More specifically, the present invention pertains to a device and method for the reduction of myocardial wall tension and the repair of mitral valve insufficiency.

Dilated cardiomyopathy is often accompanied by mitral valve insufficiency. There are several reasons for the presence of mitral valve insufficiency associated with a dilated heart. First, chamber dilation and associated high wall stresses increase the diameter of the mitral valve annulus. Additionally, as the heart dilates, the positioning of the papillary muscles is altered. Papillary muscles and chordae in a dilated heart will have moved both radially away and down from the mitral valve. This rearrangement of the vascular apparatus and enlargement of the annulus prevent the valve from closing properly.

Currently mitral valve insufficiency is treated by either repairing or replacing the valve. Surgical procedures used to repair the valve including ring posterior annuloplasty which consists of sewing a C or D-shaped ring around the posterior leaflet of the mitral valve and drawing in the annulus, reducing its previously enlarged diameter. Another method is to approximate the anterior and posterior mitral leaflets (Alfieri repair) by placing one suture through the center of both leaflets. This gives the valve a figure 8-shaped appearance when the valve is opened. When the mitral valve is replaced, the original leaflets are removed and the chordae are cut. An artificial valve consists of mechanical or tissue leaflets suspended on struts attached to a metal stent, and is sutured into place on the mitral annulus.

It has been argued that valve repair is preferable to valve replacement if the leaflet-chordae-papillary connections can be maintained. Heart wall stress will increase if the chordae are cut during valve replacement. It has been shown that by severing the chordae there can be 30 percent (30%) reduction in chamber function. Mitral valve replacement has high morality in very sick, chronic heart failure patients.

SUMMARY OF THE INVENTION

The present invention pertains to a device and method for mitral valve repair. The mitral valve is generally defined as its leaflets or cusps, but in reality, it actually consists of the entire left ventricle chamber. By creating an improved chamber geometry, both chamber and valve function will be improved. The device of the present invention and method for valve repair/replacement can include treatment for chronic heart failure by reducing left ventricular wall tension.

In one embodiment of the present invention, the valve repair device includes an elongate tension member having a first end and second end. The basal anchor is disposed at the first end and the secondary anchor is disposed at the second end.

The basal anchor could include a pad and annuloplasty ring or the like. Alternately an artificial heart valve could serve as the basal anchor.

Tension members can be substantially rigid or substantially flexible. The secondary anchor can include a hook-shaped papillary muscle tissue loop, screw-shaped tissue anchor or transmural anchor pad.

The method of the present invention providing a tension member having a first end and a second end. The tension member has a basal anchor at the first end and a secondary anchor at the second end. The basal anchor is anchored proximate to the valve such that the tension member is disposed in the chamber. The secondary anchor is anchored to a portion of the heart spaced from the basal anchor such that the tension member is under tension and the geometry of the chamber has been altered by placement of the tension member.

The basal anchor can include an artificial heart valve, annuloplasty ring or the like. The secondary anchor can be anchored to a papillary muscle or transmurally anchored.

More than one tension member can be used. Additionally, a transverse tension member can be placed across the chamber generally perpendicular to the other tension members to further alter the geometry of the heart, reducing wall stress and improving chamber performance.

DETAILED DESCRIPTION OF THE INVENTION

Figure 1:
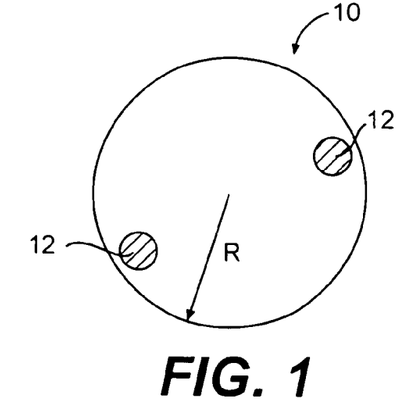
FIG. 1 is a transverse cross section of the left ventricle of a human heart taken from FIG. 2.
Figure 2:
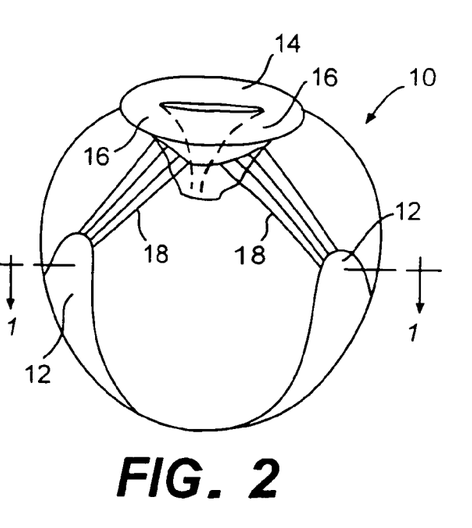
FIG. 2 is a vertical cross section of the left ventricle of a human heart.

Referring now the drawings wherein like reference numerals refer to like elements throughout the several views, FIG. 1 shows a transverse cross section of the left ventricle 10 of a failing heart taken from FIG. 2. The papillary muscles 12 are shown in cross section. FIG. 2 is a vertical cross section of human heart 10. A mitral valve is disposed near the top of left ventricle 10. Mitral valve 14 includes two leaflets or cusps 16. Chordae 18 extend between leaflets 16 and papillary muscles 12.

Figure 3:
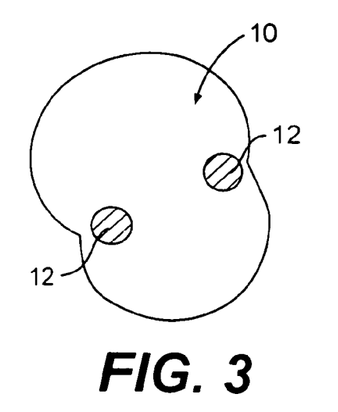
FIG. 3 is a modified, transverse, cross section of the left ventricle of a human heart taken from FIG. 4.
Figure 4:
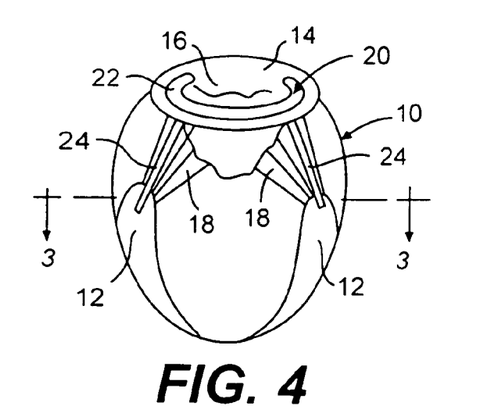
FIG. 4 is modified, vertical cross section of a human heart, modified by a device in accordance with the present invention.

FIG. 3 is a cross section of heart 10 modified from that shown in FIG. 1 by placement of valve repair device 20 in accordance with the present invention as shown in FIG. 4. FIG. 4 is a vertical cross section of left ventricle 10 with geometry modified by device 20. In this embodiment of the invention, device 20 includes a basal anchor 22 such as an annuloplasty or suture ring sewn proximate the annulus of valve 14. Extending from basal anchor 22 are elongate tension members 24. Each have a first end connected to basal anchor 22 and a second end anchored to papillary muscles 12 or the heart wall.

As can be seen in FIGS. 3 and 4, both the transverse radius and vertical dimension of left ventricle 10 has been reduced in comparison to that of FIGS. 1 and 2 by drawing papillary muscles 12 toward valve 14 with tension members 24. This change in geometry reduces heart wall stress and consequently increasing chamber function. Valve function is also improved as explained in more detail by reference to FIGS. 5 and 6.

Figure 5:
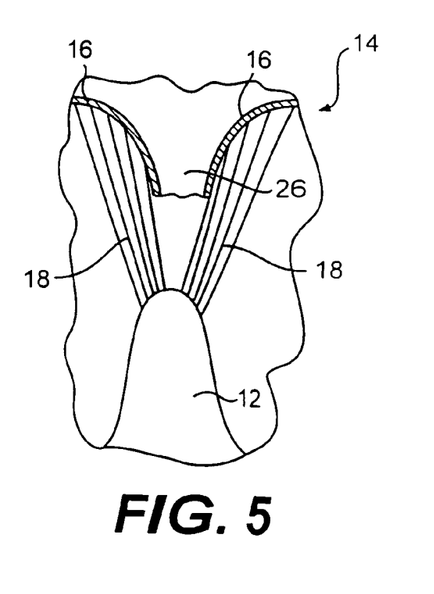
FIG. 5 is a cross section of an insufficient mitral valve of a left ventricle of a human heart.

FIG. 5 is a generally vertical cross section of an insufficient mitral valve of a heart suffering from chronic heart failure. In this case as the failing heart has dilated, papillary muscle 12 has been drawn away from mitral valve 14. The chordae connections between papillary muscles 12 and valve 14 in turn draws leaflets 16 apart such that during the normal cardiac cycle, leaflets 16 may not completely close. Thus, an opening 26 is left between leaflets 16 throughout the cardiac cycle. Opening 26 will allow blood to leak, reducing chamber efficiency.

Figure 6:
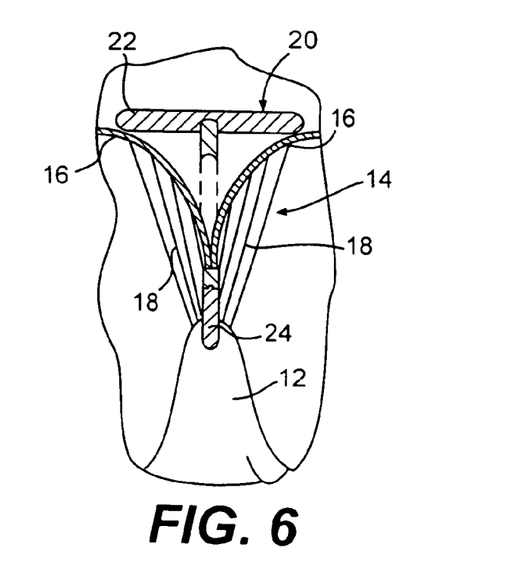
FIG. 6 is a cross section of a repaired valve and device in accordance with the present invention.

FIG. 6 is a view of the mitral valve 14 of FIG. 5 which has been modified by placement of valve repair device 20 as shown. Suture ring 22 is sewn proximate the annulus of valve 14, as known to those skilled in the use of suture rings. The annulus of valve 14 can be decreased in size by drawing the annulus toward the suture ring by the sutures used to connect ring 22 to the valve. Drawing the annulus of valve 14 toward suture ring 22 will help to eliminate opening 26. Tension member 24 is then anchored to papillary muscle 12 such that papillary muscle 12 is drawn toward valve 14. Whether or not the suture ring alone is sufficient to eliminate opening 26, drawing papillary muscle 12 toward valve 14 will provide additional stress relief on leaflet 16 promoting complete closure of valve 14. Drawing papillary muscle 12 toward 14 also reduces heart wall stress and increases chamber efficiency as discussed previously.

Figure 7:
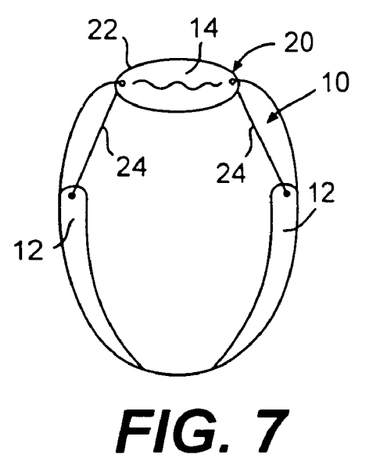
FIG. 7 is an embodiment of the device of the present invention.
Figure 8:
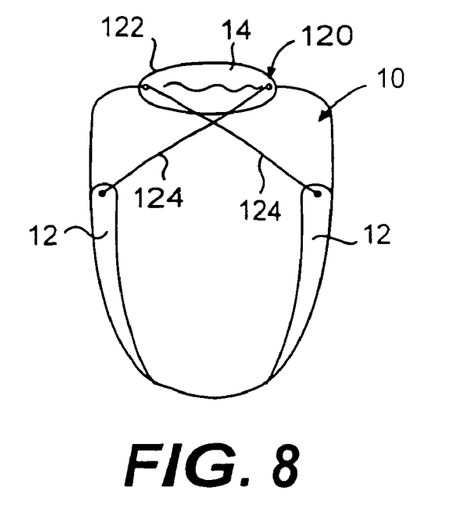
FIG. 8 is an alternate embodiment of a device in accordance with the present invention.

FIG. 7 is a highly simplified view of left ventricle 10 and valve repair device 20 as shown in FIG. 4. It can be noted that tension members 24 extend from basal anchor 22 to an adjacent papillary muscle 12. In contrast, FIG. 8 is a similar cross sectional view of left ventricle 10, but a valve repair device 120 is placed such that its tension members 124 extend between a basal anchor 122 and a papillary muscle 12 transversely opposite the point at which tension member 124 is connected to basal anchor 122. This arrangement, as opposed to that shown in FIG. 7, can increase the transverse component of the tension force in tension members 124 relative to the vertical component of that tensile force.

Figure 9:
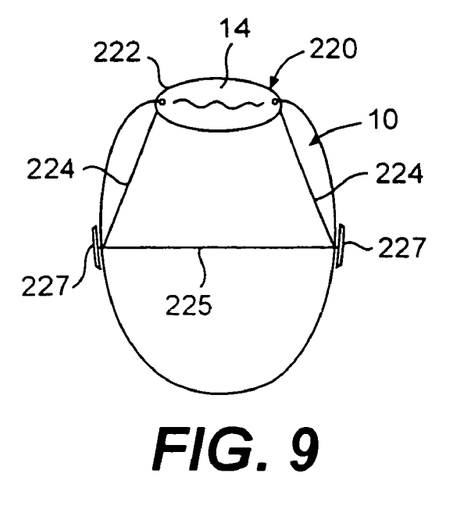
FIG. 9 is yet another alternate embodiment of a device in accordance with the present invention.

FIG. 9 shows yet another embodiment of the valve repair device in accordance with the present invention referred to by numeral 220. In this embodiment, device 220 is disposed in left ventricle 10 in a manner similar to that of device 20 shown in FIG. 7 in that tension members 224 of device 220 extend from a basal anchor 222 to an adjacent secondary anchor point. The secondary anchor point is established by transverse extension of a tension member 225 across left ventricle 10. Tension member 225 is anchored transmurally to the heart wall at its opposite ends by pads 227. In turn, tension members 224 are anchored or connected to tension member 225.

Tension member 225 can be used to further alter the geometry of left ventricle 10 in a manner disclosed in U.S. Pat. No. 5,961,440, entitled "HEART WALL TENSION REDUCTION APPARATUS AND METHOD", which was filed on Sep. 18, 1997 and is incorporated herein by reference.

Figure 10:
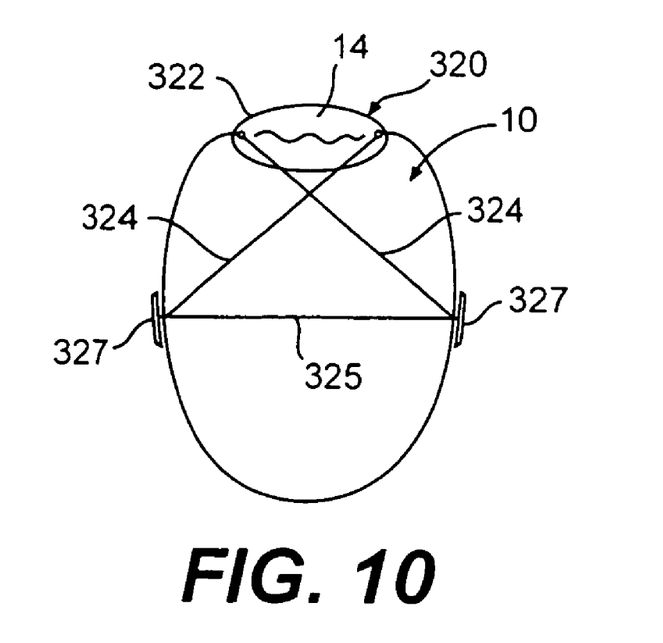
FIG. 10 is yet another alternate embodiment of the device in accordance with the present invention.

FIG. 10 shows yet another embodiment of a valve repair device in accordance with the present invention referred to by numeral 320. This embodiment includes a basal anchor 322 and tension members 324 and a transverse tension member 325 having anchor pads 327 similar to those of device 220. With respect to device 320, however, tension members 324 are crossed similar to those of device 120 of FIG. 8 to increase the horizontal component relative to the vertical component of the tensile force in tension member 324.

Figure 11:
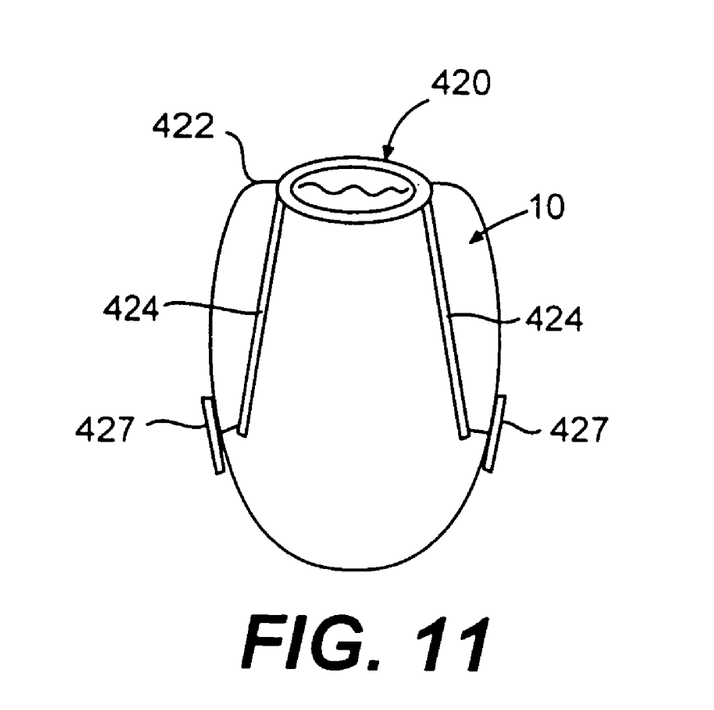
FIG. 11 is yet another alternate embodiment of a device in accordance with the present invention.

FIG. 11 is a yet another embodiment 420 of the valve repair device of the present method. Valve repair device 420 includes a basal anchor 422 and tension members 424. Tension members 424 are disposed in an arrangement similar to tension members 24 of device 20 shown in FIG. 7 except that tension members 424 are anchored transmurally by pads 427 rather than into papillary muscles 12. The relatively greater thickness of tension members 424 shown in FIG. 11, as compared to tension members 24 shown in FIG. 7, merely illustrates that the tension members can be substantially rigid or in the case of tension members 24, substantially flexible. It should be understood, however, that in any of the embodiments shown herein, the tension members could be advantageously formed to be substantially flexible or substantially rigid.

Figure 12:
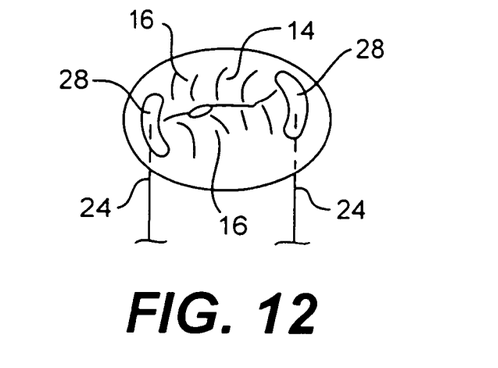
FIG. 12 is a view of a basal anchor for the device of the present invention.

FIG. 12 is a top or posterior view of valve 14. In this embodiment, the basal anchor for the valve repair device is shown as discrete pads 28 which can be sewn to the posterior side of valve 14. Tension members 24 are shown extending from respective pads 28 into the left ventricle.

Figure 13:
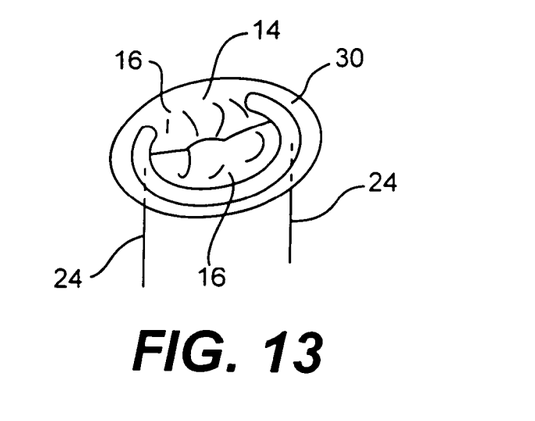
FIG. 13 is a suture ring serving as a basal anchor for the device of the present invention.

FIG. 13 is the same view of valve 14 as FIG. 12. In FIG. 13, however, the basal anchor 22 is shown as a crescent-shaped suture ring. Tension members 24 extends from basal anchor 22 through valve 14 into the left ventricle.

Figure 14:
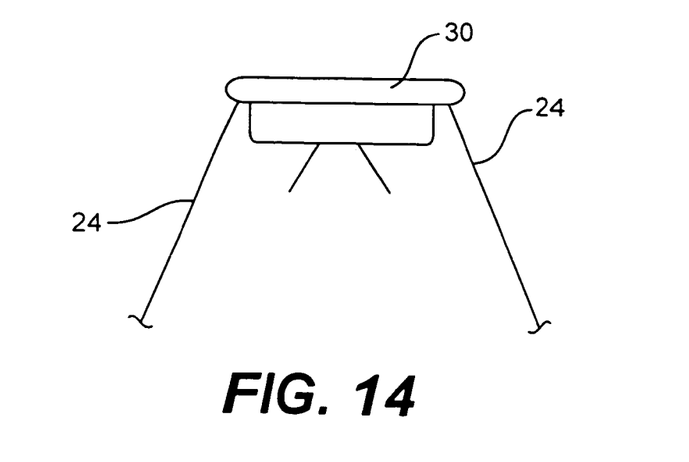
FIG. 14 is a replacement valve serving as a anchor for the device of the present invention.

FIG. 14 is a side view of an artificial heart valve 30. If it is necessary to replace the valve rather than merely repair it, artificial valve 30 can be used as a basal anchor for tension members 24.

Figure 15:
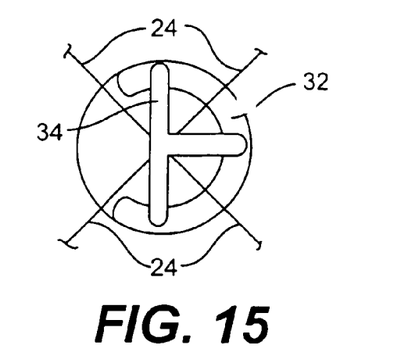
FIG. 15 is a top view of an alternate embodiment of a suture ring acting as an anchor for the device of the present invention.
Figure 16:
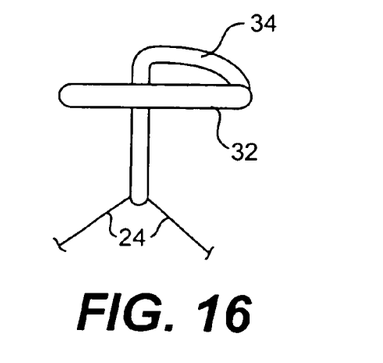
FIG. 16 is a side view of the suture ring of FIG. 15.

FIG. 15 is a top view of an alternate embodiment of a suture ring basal anchor 32. Ring 32 has a crescent shape and a pylon 34 extending through the mitral valve. FIG. 16 is a side view of suture ring 32 showing tension members 24 attached to pylon 34.

Tension members 24 preferably extend through the tissue of valve 14 rather than through the valve opening. It can be appreciated, however, that tension members 24 could be disposed through the valve opening. In the case of the embodiment of FIGS. 15 and 16, however, pylon 34 would be disposed through the valve opening. Tension members 24 associated with pylon 34 would be disposed on the opposite side of valve 14 from suture ring 32. Pylon 34 would preferably be disposed through the valve opening rather than the tissue forming valve 14.

Figure 17:
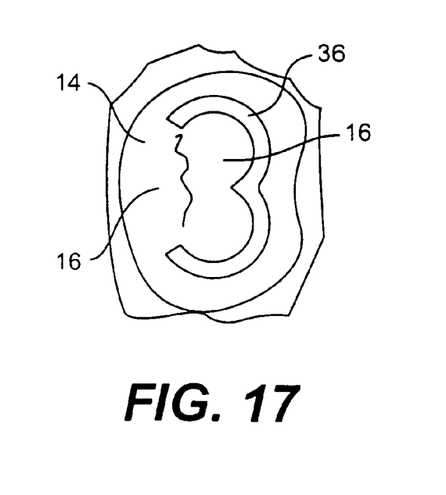
FIG. 17 is a view of an alternate embodiment of a suture ring which can act as basal anchor for the device of the present invention.
Figure 18:
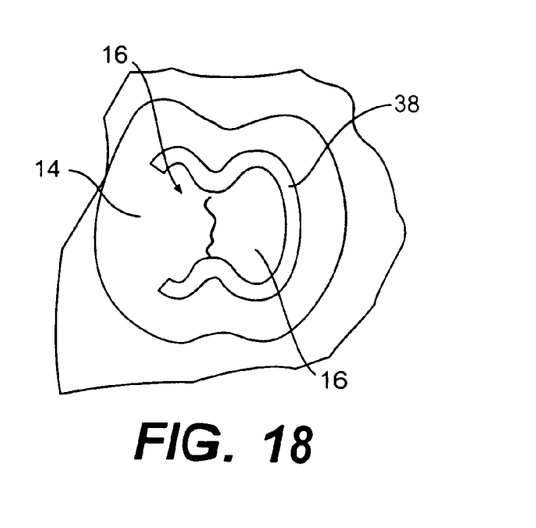
FIG. 18 is a view of yet another alternate embodiment of a suture ring which can act as a basal anchor for the present invention.

FIGS. 17 and 18 are yet additional alternate embodiments of suture rings which can be used as basal anchors in accordance with the present invention. The shape of the rings is selected such that as they are sewn into place on valve 14, the sutures can be used to draw tissue toward the inside of the ring, thus reducing the transverse and/or vertical cross sectional area of the associated heart chamber. This will advantageously reduce heart wall stress which is of particular benefit if the patient has a failing heart.

It can be appreciated that tension members 24 can be fixably or releasably attached to the basal anchor. Preferably, the tension members are fixably attached to the basal anchor during the valve repair procedure.

Figure 19:
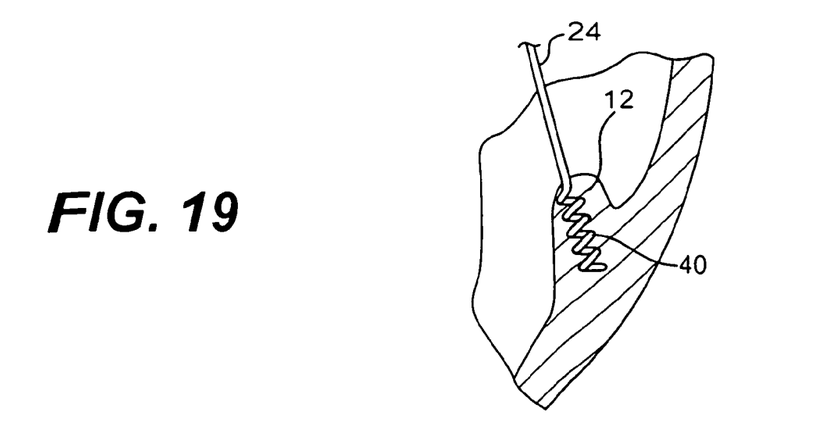
FIG. 19 is a embodiment of a secondary anchor for the device of the present invention.
Figure 20:
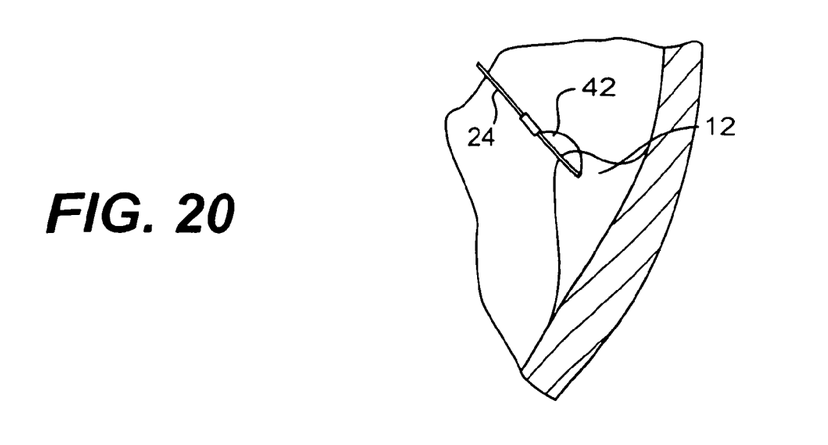
FIG. 20 is a view of an alternate embodiment of a secondary anchor for the device of the present invention.
Figure 21:
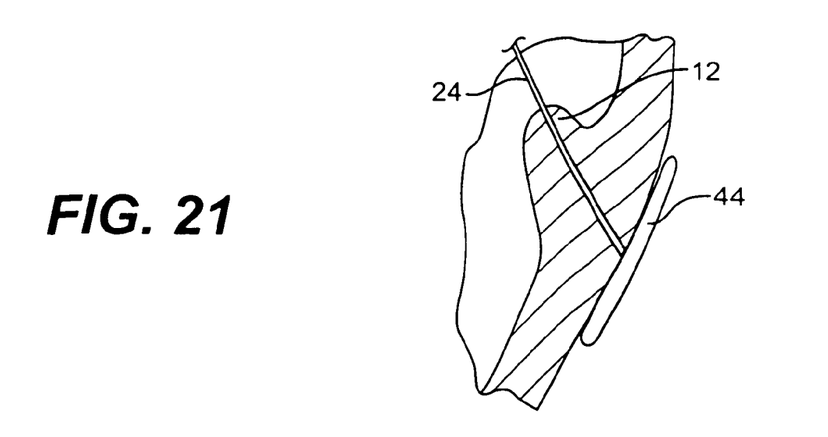
FIG. 21 is yet another embodiment of a secondary anchor for the device of the present invention.

FIGS. 19-21 show various configurations of anchoring devices shown at the second end of tension member 24. It can be appreciated that these anchoring devices could be used with each of the tension members described above. In FIG. 19, the second end of tension member 24 includes a secondary anchor 40 formed as screw which is shown augured into papillary muscle 12. FIG. 20 shows a secondary anchor 42 including a loop sewn through papillary muscle 12. FIG. 21 shows a tension member 24 extending transmurally to an exterior pad 44 to which it is connected. Tension member 24 could be sewn to pad 44 or otherwise mechanically connected thereto.

It can be appreciated that various biocompatible materials can be advantageously used to form the various components of the device of the present invention. It is anticipated that the present device will usually be chronically implanted. Thus, when selecting materials to form each of the components consideration should be given to the consequences of long term exposure of the device to tissue and tissue to the device.

Numerous characteristics and advantages of the invention covered by this document have been set forth in the foregoing description. It will be understood, however, that this disclosure is, in many respects, only illustrative. Changes may be made in details, particularly in matters of shape, size, and arrangement of parts without exceeding the scope of the invention. The inventions's scope is, of course, defined in the language in which the appended claims are expressed.

What is claimed is:

1. A method of treating an in situ mitral valve, comprising:
providing a valve repair device to be secured to a mitral valve annulus, the device including a basal anchor adapted to attach around at least a portion of the mitral valve annulus and having a pylon fixed thereto that extends through the mitral valve opening into the left ventricle associated with the mitral valve, the device further including tension members attached to the pylon within the left ventricle and each having a length sufficient to extend to a papillary muscle within the left ventricle, the device further including an anchor corresponding to each tension member for securing the tension member to the respective papillary muscle;
delivering the device to the mitral valve annulus;
anchoring the tension members to respective papillary muscles using the corresponding anchors;
securing the basal anchor to the mitral valve annulus; and
establishing tension in the tension members between the respective papillary muscles and the basal anchor.

2. The method of claim 1, wherein the basal anchor is crescent-shaped.

3. The method of claim 2, wherein the pylon is fixed to at least two points on the basal anchor and has a spanning portion that spans between the two points and across the mitral valve opening above the basal anchor, the pylon further including a descending portion that extends through the mitral valve opening into the left ventricle associated with the mitral valve and to which the tension members attach.

4. The method of claim 3, wherein the pylon further includes a perpendicular portion that bisects the spanning portion over the mitral valve opening and extends perpendicularly therefrom to a third point on the basal anchor, such that the descending portion is supported by a T-shaped structure over the mitral valve opening.

5. The method of claim 1, wherein establishing tension in the tension members reduces one or both of the transverse radius and vertical dimension of the left ventricle.

6. The method of claim 1, wherein establishing tension in the tension members draws the papillary muscles toward the basal anchor.

7. The method of claim 1, wherein the tension members are fixably attached to the basal anchor.

8. The method of claim 1, wherein the tension members are releasably attached to the basal anchor.

9. The method of claim 1, further including placing a transverse tension member across the ventricular cavity and between the papillary muscles to which the tension members anchor and establishing tension in the transverse tension member directly between the papillary muscles.

10. The method of claim 1, wherein the anchors for securing the tension members to the papillary muscles are transmural anchor pads.

11. The method of claim 1, wherein the anchors for securing the tension members to the papillary muscles are hook-shaped papillary muscle tissue loops.

12. The method of claim 1, wherein the anchors for securing the tension members to the papillary muscles are screw-shaped tissue anchors.

13. The method of claim 1, wherein the tension members are substantially flexible.

14. The method of claim 1, wherein the tension members are substantially rigid.

15. The method of claim 1, wherein securing the basal anchor to the mitral valve annulus comprises sewing the basal anchor to the mitral valve annulus.

16. The method of claim 15, wherein securing the basal anchor to the mitral valve annulus decreases the size of the annulus.

17. The method of claim 1, wherein the basal anchor is an annuloplasty ring.

18. A method of treating an in situ mitral valve, comprising:
providing a valve repair device to be secured to a mitral valve annulus, the device including a generally planar basal anchor adapted to attach around at least a portion of the mitral valve annulus and having a pylon fixed to at least two points on the basal anchor and having a spanning portion that spans between the two points and across the mitral valve opening above the planar basal anchor, the pylon further including a descending portion that extends through the mitral valve opening into the left ventricle associated with the mitral valve;
delivering the device to the mitral valve annulus;

tethering a distal end of the pylon descending portion within the left ventricle to a papillary muscle using a flexible elongate member;

securing the basal anchor to the mitral valve annulus; and establishing tension in the flexible elongate member between the papillary muscle and the basal anchor.

19. The method of claim 18, wherein the basal anchor is crescent-shaped.

20. The method of claim 18, wherein the pylon further includes a perpendicular portion that bisects the spanning portion over the mitral valve opening and extends perpendicularly therefrom to a third point on the basal anchor, such that the descending portion is supported by a T-shaped structure over the mitral valve opening.

21. The method of claim 18, wherein establishing tension in the flexible elongate member reduces one or both of the transverse radius and vertical dimension of the left ventricle.

22. The method of claim 18, wherein establishing tension in the flexible elongate member draws the papillary muscle toward the basal anchor.

23. The method of claim 18, wherein the flexible elongate member is fixably attached to the basal anchor.

24. The method of claim 18, wherein the flexible elongate member is releasably attached to the basal anchor.

25. The method of claim 18, wherein there are two flexible elongate members attached to the pylon within the left ventricle and each having a length sufficient to extend to a papillary muscle within the left ventricle.

26. The method of claim 25, further including placing a transverse flexible elongate member across the ventricular cavity and between the papillary muscles to which the flexible elongate members anchor and establishing tension in the transverse flexible elongate member directly between the papillary muscles.

27. The method of claim 18, wherein the device further includes an anchor for securing the flexible elongate member to the papillary muscle.

28. The method of claim 27, wherein the anchor is a transmural anchor pad.

29. The method of claim 27, wherein the anchor is a hook-shaped papillary muscle tissue loop.

30. The method of claim 27, wherein the anchor is a screw-shaped tissue anchor.

31. The method of claim 18, wherein the flexible elongate member is substantially flexible.

32. The method of claim 18, wherein the flexible elongate member is substantially rigid.

33. The method of claim 18, wherein securing the basal anchor to the mitral valve annulus comprises sewing the basal anchor to the mitral valve annulus.

34. The method of claim 33, wherein securing the basal anchor to the mitral valve annulus decreases the size of the annulus.

35. The method of claim 18, wherein the basal anchor is an annuloplasty ring.

* * * * *